United States Patent
Reik et al.

(10) Patent No.: US 10,907,175 B2
(45) Date of Patent: *Feb. 2, 2021

(54) ISOLATED HUMAN CELL WITH AN INACTIVATED GLUCOCORTICOID RECEPTOR GENE

(71) Applicants: Sangamo BioSciences, Inc., Richmond, CA (US); City of Hope, Duarte, CA (US)

(72) Inventors: Andreas Reik, Vallejo, CA (US); Michael Jensen, Sierra Madre, CA (US); Michael C. Holmes, Oakland, CA (US); Philip D. Gregory, Orinda, CA (US); Dale Ando, Walnut Creek, CA (US)

(73) Assignees: Sangamo Therapeutics, Inc., Brisbane, CA (US); City of Hope, Duarte, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/947,476

(22) Filed: Nov. 20, 2015

(65) Prior Publication Data

US 2016/0076056 A1 Mar. 17, 2016

Related U.S. Application Data

(63) Continuation of application No. 11/983,888, filed on Nov. 13, 2007, now Pat. No. 9,217,026.

(60) Provisional application No. 60/859,025, filed on Nov. 13, 2006, provisional application No. 60/859,417, filed on Nov. 15, 2006, provisional application No. 60/967,820, filed on Sep. 7, 2007.

(51) Int. Cl.

| | |
|---|---|
| *C12N 5/00* | (2006.01) |
| *C12N 15/00* | (2006.01) |
| *C12N 5/02* | (2006.01) |
| *C12N 15/86* | (2006.01) |
| *C12N 15/62* | (2006.01) |
| *C07K 14/72* | (2006.01) |
| *C12N 9/22* | (2006.01) |
| *G01N 33/74* | (2006.01) |

(52) U.S. Cl.
CPC ............ *C12N 15/86* (2013.01); *C07K 14/721* (2013.01); *C12N 9/22* (2013.01); *C12N 15/62* (2013.01); *G01N 33/743* (2013.01); *C12N 2710/10043* (2013.01); *C12N 2740/15043* (2013.01); *G01N 2333/723* (2013.01)

(58) Field of Classification Search
USPC ........................................ 435/325; 424/93.21
See application file for complete search history.

(56) References Cited

U.S. PATENT DOCUMENTS

| | | | |
|---|---|---|---|
| 5,436,150 A | 7/1995 | Chandrasegaran | |
| 5,789,538 A * | 8/1998 | Rebar ................ | C07K 14/4705 530/300 |
| 5,925,523 A * | 7/1999 | Dove ................. | C12N 15/1055 435/29 |
| 6,007,988 A * | 12/1999 | Choo ................. | C07K 14/4702 435/6.12 |
| 6,013,453 A * | 1/2000 | Choo ................. | C07K 14/4702 506/17 |
| 6,140,081 A * | 10/2000 | Barbas ..................... | C07K 7/08 435/252.2 |
| 6,140,466 A | 10/2000 | Barbas et al. | |
| 6,200,759 B1 * | 3/2001 | Dove ................. | C12N 15/1055 435/6.16 |
| 6,410,248 B1 * | 6/2002 | Greisman .......... | C12N 15/1037 435/4 |
| 6,453,242 B1 * | 9/2002 | Eisenberg .............. | C07K 14/47 435/6.18 |
| 6,534,261 B1 * | 3/2003 | Cox, III ............. | G01N 33/5091 435/29 |
| 6,733,970 B2 * | 5/2004 | Choo ................. | C12N 15/1041 435/6.12 |
| 6,746,838 B1 * | 6/2004 | Choo ..................... | C07K 1/047 435/6.12 |
| 6,784,136 B2 * | 8/2004 | Iwasaki ................ | B41M 5/3333 503/200 |
| 6,785,613 B2 * | 8/2004 | Eisenberg .............. | C07K 14/47 435/6.11 |
| 6,794,136 B1 | 9/2004 | Eisenberg et al. | |
| 6,866,997 B1 * | 3/2005 | Choo ..................... | C07K 1/047 435/6.12 |
| 6,933,113 B2 | 8/2005 | Case et al. | |
| 7,030,215 B2 * | 4/2006 | Liu .......................... | C07K 1/00 435/6.12 |

(Continued)

FOREIGN PATENT DOCUMENTS

| | | |
|---|---|---|
| WO | WO 95/19431 A1 | 7/1995 |
| WO | WO 96/06166 * | 2/1996 |

(Continued)

OTHER PUBLICATIONS

Chandrasegaran (Biol. Chem., 1999, vol. 380, p. 841-848).*

(Continued)

*Primary Examiner* — Michael C Wilson

(74) *Attorney, Agent, or Firm* — Pasternak Patent Law

(57) ABSTRACT

Disclosed herein are methods and compositions for inactivation of the human glucocorticoid receptor (GR) gene by targeted cleavage of genomic DNA encoding the GR. Such methods and compositions are useful, for example, in therapeutic applications which require retention of immune function during glucocorticoid treatment.

7 Claims, 15 Drawing Sheets

Specification includes a Sequence Listing.

(56) References Cited

U.S. PATENT DOCUMENTS

| | | | |
|---|---|---|---|
| 7,407,776 B2 | 8/2008 | Moore et al. | |
| 7,510,868 B2 | 3/2009 | Harden et al. | |
| 7,914,796 B2 * | 3/2011 | Miller | C12N 9/22 424/192.1 |
| 2003/0044957 A1 * | 3/2003 | Jamieson | C07K 14/4702 435/219 |
| 2003/0092000 A1 * | 5/2003 | Eisenberg | C07K 14/47 435/6.12 |
| 2003/0108880 A1 * | 6/2003 | Rebar | C07K 14/4702 435/6.12 |
| 2003/0134318 A1 * | 7/2003 | Case | C12N 15/1079 435/6.18 |
| 2003/0171546 A1 | 9/2003 | Jensen | |
| 2003/0232410 A1 | 12/2003 | Liljedahl et al. | |
| 2004/0019002 A1 * | 1/2004 | Choulika | C12N 15/902 514/44 R |
| 2004/0128717 A1 * | 7/2004 | Jamieson | C12N 15/8217 800/280 |
| 2005/0026157 A1 | 2/2005 | Baltimore | |
| 2005/0064474 A1 * | 3/2005 | Urnov | C07K 14/43595 435/6.18 |
| 2005/0129671 A1 | 6/2005 | Cooper et al. | |
| 2005/0208489 A1 | 9/2005 | Carroll | |
| 2006/0067920 A1 | 3/2006 | Jensen | |
| 2006/0188987 A1 | 8/2006 | Guschan et al. | |
| 2007/0134796 A1 | 6/2007 | Holmes et al. | |

FOREIGN PATENT DOCUMENTS

| | | | |
|---|---|---|---|
| WO | WO 96/06166 A1 | | 2/1996 |
| WO | WO 98/53057 | * | 11/1998 |
| WO | WO 98/53057 A1 | | 11/1998 |
| WO | WO 98/53058 | * | 11/1998 |
| WO | WO 98/53058 A1 | | 11/1998 |
| WO | WO 98/53059 | * | 11/1998 |
| WO | WO 98/53059 A1 | | 11/1998 |
| WO | WO 98/53060 | * | 11/1998 |
| WO | WO 98/53060 A1 | | 11/1998 |
| WO | WO 98/54311 | * | 12/1998 |
| WO | WO 98/54311 A1 | | 12/1998 |
| WO | WO 00/27878 | * | 5/2000 |
| WO | WO 00/27878 A1 | | 5/2000 |
| WO | WO 01/53480 | * | 7/2001 |
| WO | WO 01/053480 A1 | | 7/2001 |
| WO | WO 01/60970 | * | 8/2001 |
| WO | WO 01/060970 A2 | | 8/2001 |
| WO | WO 01/88197 | * | 11/2001 |
| WO | WO 01/088197 A2 | | 11/2001 |
| WO | WO 02/016536 | * | 2/2002 |
| WO | WO 02/016536 A1 | | 2/2002 |
| WO | WO 02/099084 | * | 12/2002 |
| WO | WO 02/099084 A2 | | 12/2002 |
| WO | WO 03/016496 A2 | | 2/2003 |
| WO | WO 05/084190 A2 | | 9/2005 |
| WO | WO 07/139898 A2 | | 12/2007 |
| WO | WO 07/139982 A2 | | 12/2007 |

OTHER PUBLICATIONS

Smith (Nucleic Acids Research 2000, vol. 28, No. 17, p. 3361-3369).*
Bibikova (MCB, Jan. 2001, vol. 21, No. 1, p. 289-297).*
Porteus (Nature Biotech., 2005, vol. 23, No. 8, p. 967-973).*
Wu (Cell Mol. Lif Science, 2007, vol. 64, 2933-2944).*
Santiago (PNAS, Apr. 2008, vol. 105, No. 15, p. 5809-5814).*
Doyon (Nature Biotech., Jun. 2008, vol. 26, No. 6, p. 702-708).*
Perez (Nature Biotech., Jul. 2008, vol. 26, No. 6, p. 808-816).*
Carroll (Gene Therapy, Sep. 11, 2008, vol. 15, p. 1463-1468).*
Beumer (PNAS, Dec. 16, 2008, vol. 105, No. 50, p. 19821-19826).*
Geurts (Science, Jul. 24, 2009, vol. 325, No. 5939, p. 433-435, and Supplemental Materials associated therewith).*
Remy (Transgenic Res. Published online Sep. 26, 2009, vol. 19, p. 363-371).*
Mashimo (PLoS One, Jan. 2010, vol. 5, No. 1, e8870, p. 1-7).*
Urnov (Nature Reviews Genetics, Sep. 2010, vol. 11, p. 636-646).*
Zhou (Steroids, 2005, vol. 70, No. 5-7, p. 407-417).*
Hillmann (Cancer Res. 2000, vol. 60, No. 7, p. 2056-2062).*
Rhen (N. Engl. J. Med., 2005, vol. 353, No. 16, p. 1711-1723).*
Bartsevich, et al., "Engineered Zinc Finger Proteins for Controlling Stem Cell Fate," *Stem Cells* 21:632-637 (2003).
Bibikova, et al., "Stimulation of Homologous Recombination Through Targeted Cleavage by Chimeric Nucleases," *Mol. Cell Biol.* 21:289-297 (2001).
Deonarain, "Ligand-Targeted Receptor-Mediated Vectors for Gene Therapy," *Expert Opin. Ther. Pat.* 8:53-69 (1998).
Edelstein, et al., "Gene Therapy Clinical Trials Worldwide 1989-2004—An Overview," *Journal Gene Med.* 6(6):597-602 (2004).
Hacein-Bey-Abina, et al., "LMO2-Associated Clonal T Cell Proliferation in Two Patients After Gene Therapy for SCID-X1," *Science* 302(5644):415-419 (2003).
High, "Gene Therapy: The Moving Finger," *Nature* 435:577-579 (2005).
Hillmann, et al., "Glucocorticoid Receptor Gene Mutations in Leukemic Cells Acquired In Vitro and In Vivo," *Cancer Res.* 60(7):2056-2062 (2000).
Johnson-Saliba, "Gene Therapy: Optimising DNA Delivery to the Nucleus," *Curr. Drug Targets* 2:371-399 (2001).
Kahlon, et al., "Specific Recognition and Killing of Glioblastoma Multiforme by Interleukin 13-Zetakine Redirected Cytolytic T Cells," *Cancer Res.* 64:9160-9166 (2004).
Li, et al., "In Vivo Genome Editing Restores Haemostasis in a Mouse Model of Haemophilia," *Nature* 475(7355):217-221 (2011).
Luo, et al., "Synthetic DNA Delivery Systems," *Nature Biotechnol.* 18:33-37 (2008).
Palu, et al., "In Pursuit of New Developments for Gene Therapy of Human Diseases," *J. Biotechnol.* 68(1):1-13 (1999).
Pfeifer, et al., "Gene Therapy: Promises and Problems," *Annu. Rev. Genomics Hum. Genet.* 2:177-211 (2001).
Porteus, et al., "Gene Targeting Using Zinc Finger Nucleases," *Nature Biotechnology* 23(8):967-973.
Porteus, et al., "Mammalian Gene Targeting With Designed Zinc Finger Nucleases," *Mol. Ther.* 2:438-446 (2006).
Ramirez, et al., "Unexpected Failure Rates for Modular Assembly of Engineered Zinc Fingers," *Nature Methods* 5(5):374-375 (2008).
Rhen, et al., "Antiinflammatory Action of Glucocorticoids—New Mechanisms for Old Drugs," *New Eng. J. Med.* 353(16):1711-1723 (2005).
Shoji, et al., "Current Status of Delivery Systems to Improve Target Efficacy of Oligonu-cleotides," *Current Pharmaceutical Design* 10:785-796 (2004).
Smith, et al., "Requirements for Double-Strand Cleavage by Chimeric Restriction Enzymes With Zinc Finger DNA-Recognition Domains," *Nucleic Acids Research* 28(17):3361-3369 (2000).
Urnov, et al., "Highly Efficient Endogenous Human Gene Correction Using Designed Zinc-Finger Nucleases," *Nature* 435:646-651 (2005).
Vanamee, et al., "Glucocorticoid Receptor-Like Zn(Cys) Motifs in BS/I Restriction Endonuclease," *J. Mol. Biol.* 334:595-603 (2003).
Verma, et al., "Gene Therapy—Promises, Problems and Prospects," *Nature* 389:239-242 (1997).
Yanez, et al., "Therapeutic Gene Targeting," *Gene Therapy* 5:149-159 (1998).
Zhou, et al., "The Human Glucocorticoid Receptor: One Gene, Multiple Proteins and Diverse Responses," *Steroids* 70:407-417 (2005).

* cited by examiner

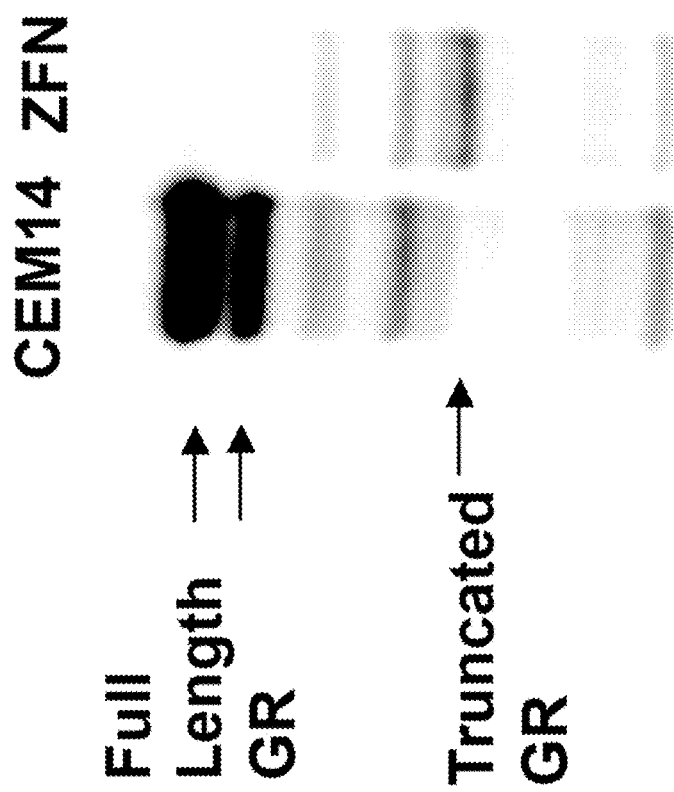

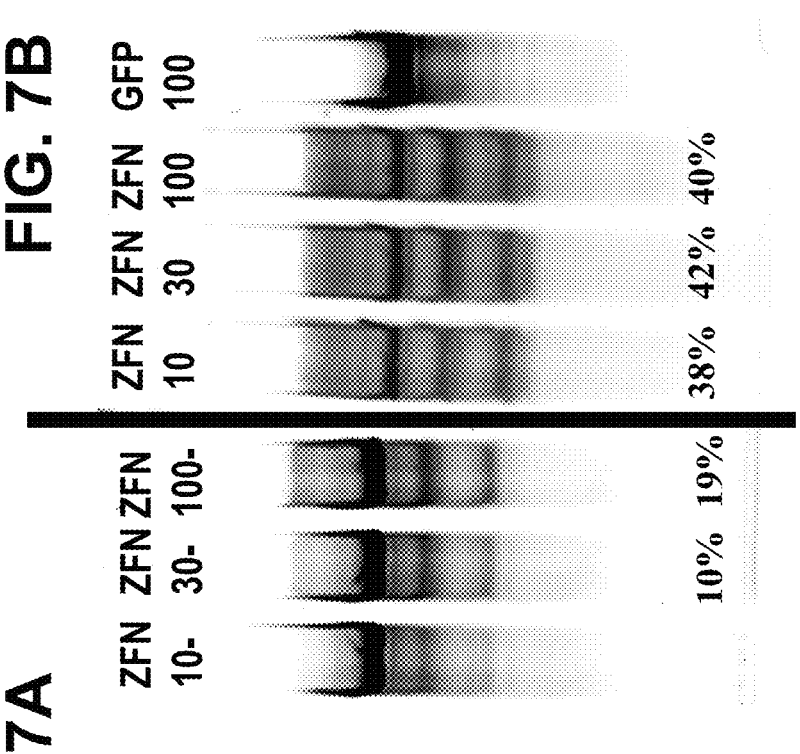

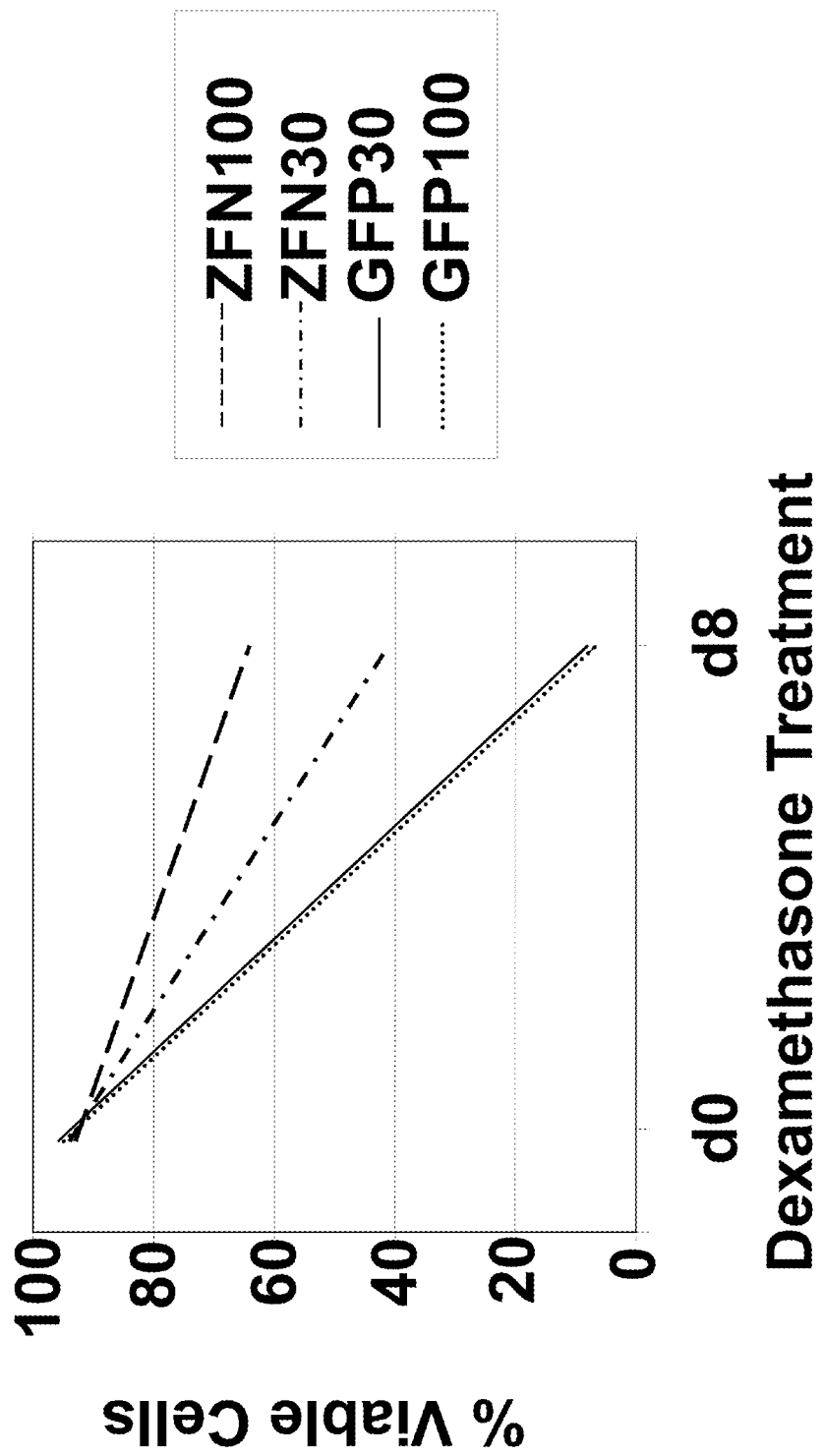

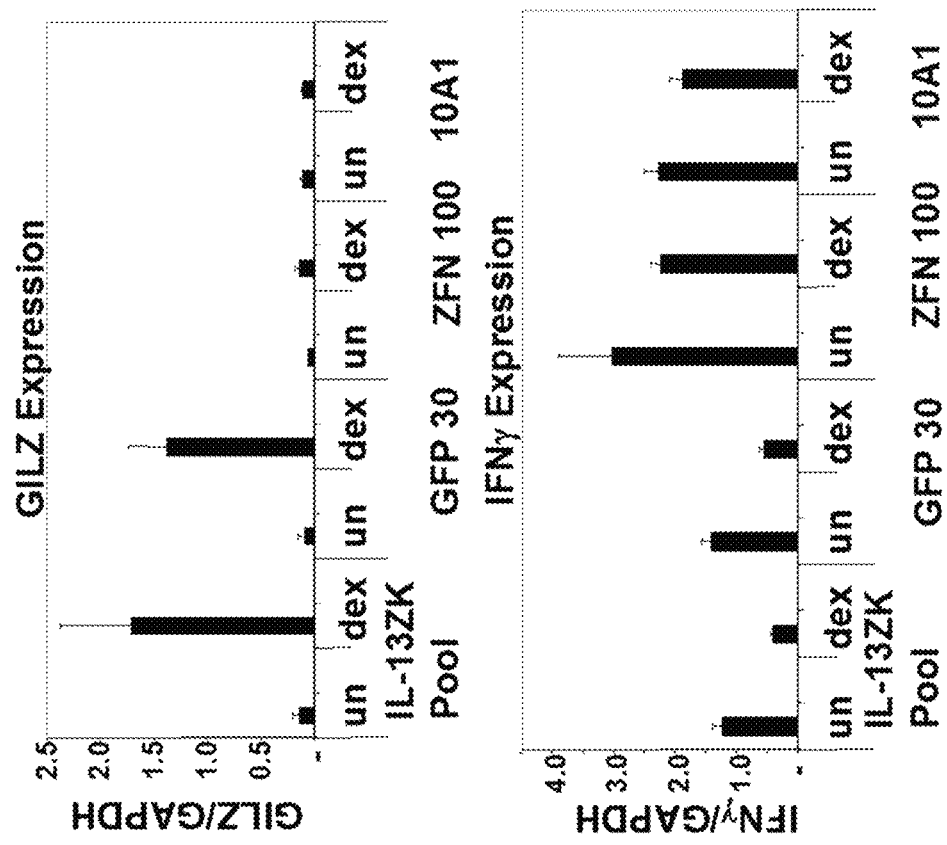
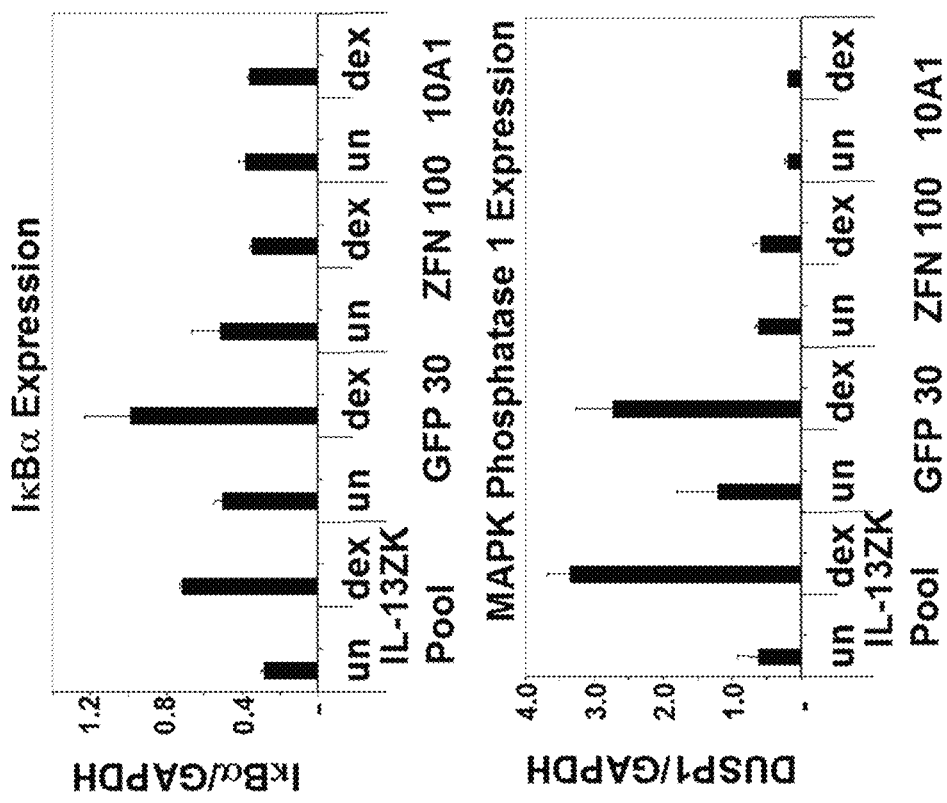
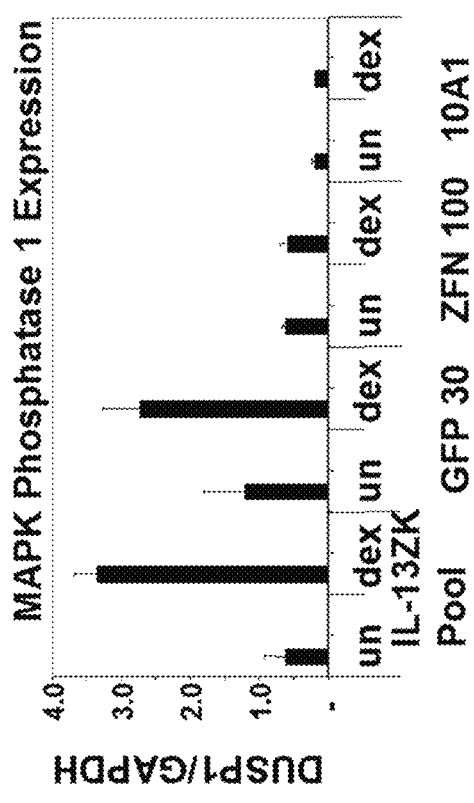

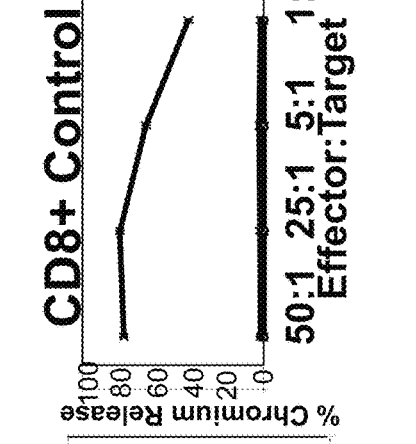
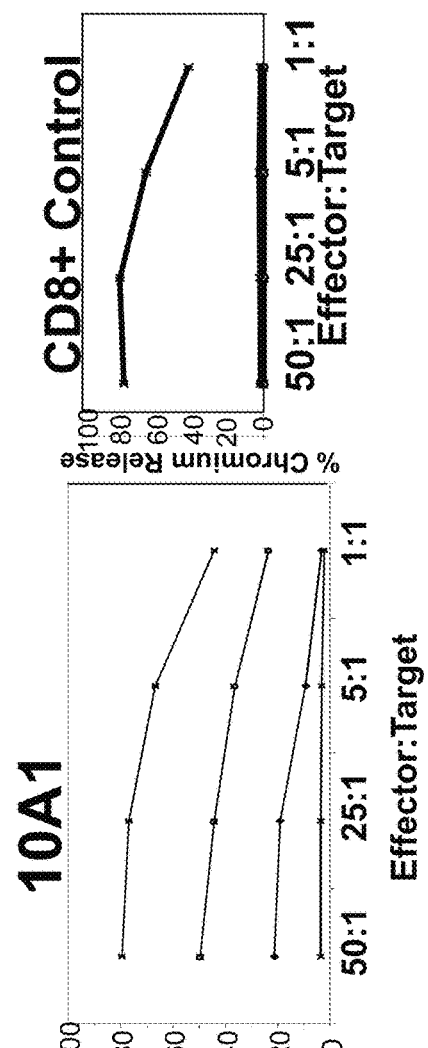
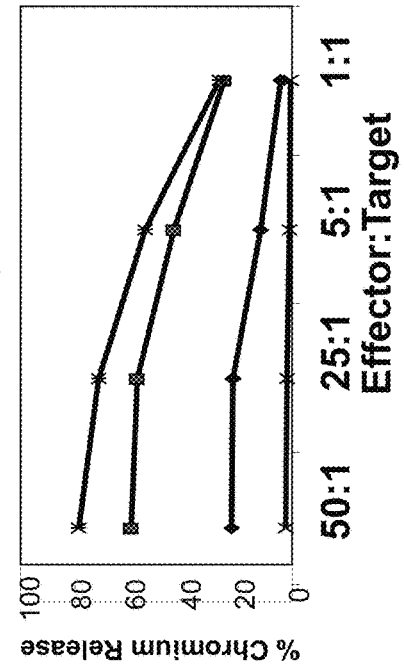
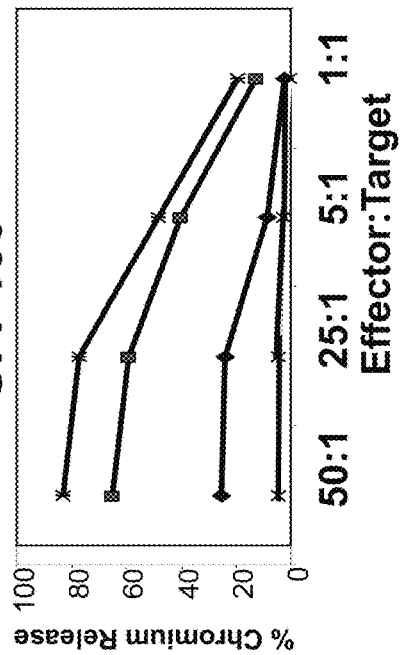
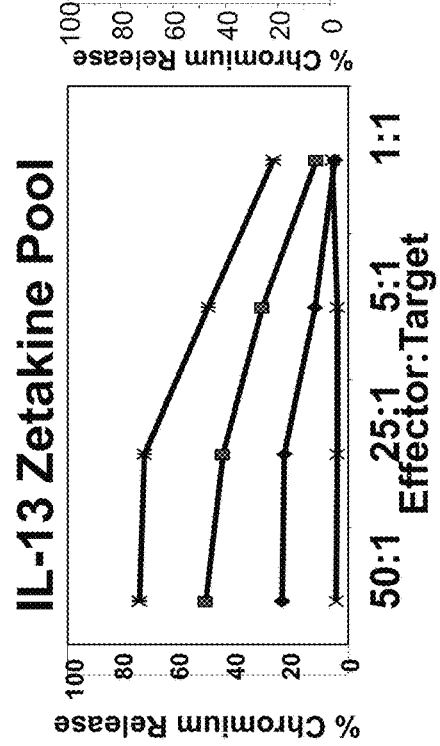

PBS control

GFP 100

ZFN 100

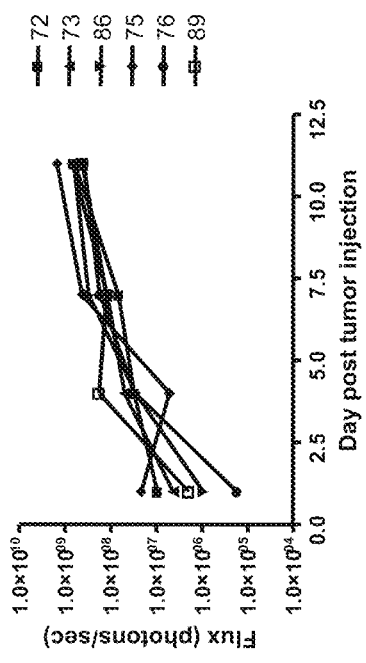
FIG. 14A: PBS-Dex
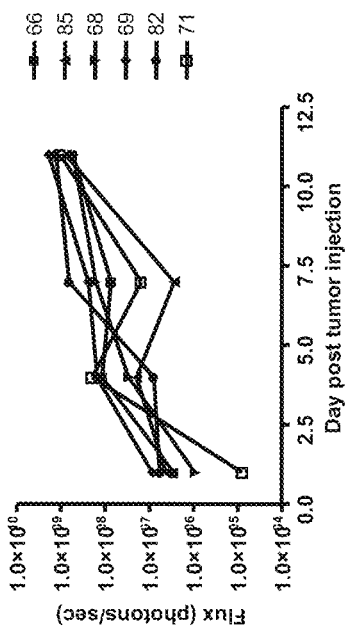
FIG. 14B: PBS+Dex
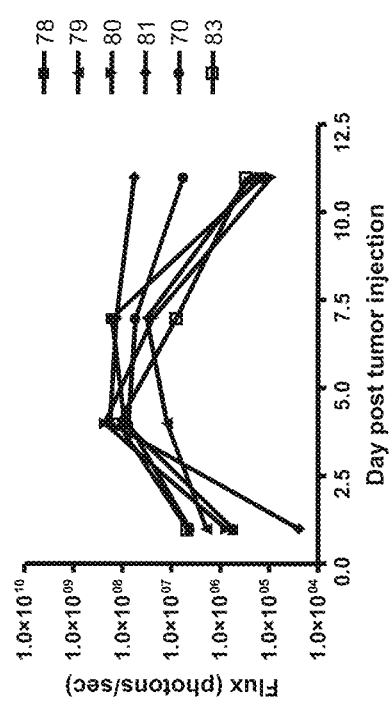
FIG. 14C: ZFN-Dex
FIG. 14D: ZFN+Dex

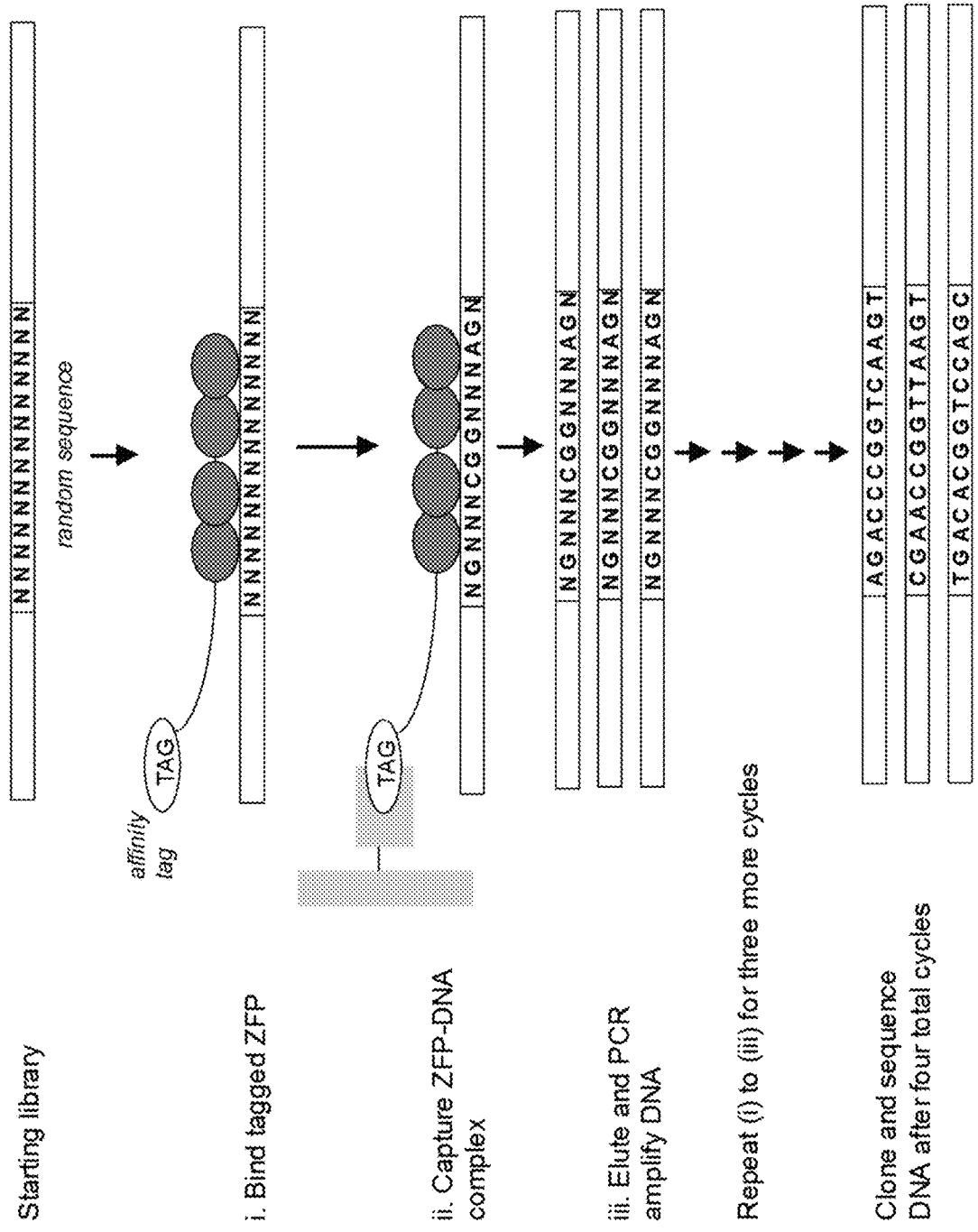

SEQUENCE LISTING

```
<160> NUMBER OF SEQ ID NOS: 57

<210> SEQ ID NO 1
<211> LENGTH: 13
<212> TYPE: DNA
<213> ORGANISM: Artificial
<220> FEATURE:
<223> OTHER INFORMATION: human glucocorticoid receptor gene target
      sequence for ZFN

<400> SEQUENCE: 1
gacctgttga tag                                                         13

<210> SEQ ID NO 2
<211> LENGTH: 16
<212> TYPE: DNA
<213> ORGANISM: Artificial
<220> FEATURE:
<223> OTHER INFORMATION: human glucocorticoid receptor gene target
      sequence for ZFN

<400> SEQUENCE: 2
gacctgttga tagatg                                                      16

<210> SEQ ID NO 3
<211> LENGTH: 12
<212> TYPE: DNA
<213> ORGANISM: Artificial
<220> FEATURE:
<223> OTHER INFORMATION: human glucocorticoid receptor gene target
      sequence for ZFN

<400> SEQUENCE: 3
tccaaggact ct                                                          12

<210> SEQ ID NO 4
```

```
<211> LENGTH: 12
<212> TYPE: DNA
<213> ORGANISM: Artificial
<220> FEATURE:
<223> OTHER INFORMATION: human glucocorticoid receptor gene target
      sequence for ZFN

<400> SEQUENCE: 4
caacaggacc ac                                                         12

<210> SEQ ID NO 5
<211> LENGTH: 12
<212> TYPE: DNA
<213> ORGANISM: Artificial
<220> FEATURE:
<223> OTHER INFORMATION: human glucocorticoid receptor gene target
      sequence for ZFN

<400> SEQUENCE: 5
gttgaggagc tg                                                         12

<210> SEQ ID NO 6
<211> LENGTH: 13
<212> TYPE: DNA
<213> ORGANISM: Artificial
<220> FEATURE:
<223> OTHER INFORMATION: human glucocorticoid receptor gene target
      sequence for ZFN

<400> SEQUENCE: 6
aatgagtaag ttg                                                        13

<210> SEQ ID NO 7
<211> LENGTH: 12
<212> TYPE: DNA
<213> ORGANISM: Artificial
<220> FEATURE:
<223> OTHER INFORMATION: human glucocorticoid receptor gene target
      sequence for ZFN

<400> SEQUENCE: 7
tcagatcagg ag                                                         12

<210> SEQ ID NO 8
<211> LENGTH: 7
<212> TYPE: PRT
<213> ORGANISM: Artificial
<220> FEATURE:
<223> OTHER INFORMATION: recognition region of glucocorticoid receptor-
      targeted ZFN

<400> SEQUENCE: 8

Arg Ser Asp Tyr Leu Ser Thr
1               5

<210> SEQ ID NO 9
<211> LENGTH: 7
<212> TYPE: PRT
<213> ORGANISM: Artificial
<220> FEATURE:
<223> OTHER INFORMATION: recognition region of glucocorticoid receptor-
      targeted ZFN

<400> SEQUENCE: 9

Gln Asn Ala His Arg Lys Thr
1               5
```

```
<210> SEQ ID NO 10
<211> LENGTH: 7
<212> TYPE: PRT
<213> ORGANISM: Artificial
<220> FEATURE:
<223> OTHER INFORMATION: recognition region of glucocorticoid receptor-
      targeted ZFN

<400> SEQUENCE: 10

Arg Ser Asp Val Leu Ser Ala
1               5

<210> SEQ ID NO 11
<211> LENGTH: 7
<212> TYPE: PRT
<213> ORGANISM: Artificial
<220> FEATURE:
<223> OTHER INFORMATION: recognition region of glucocorticoid receptor-
      targeted ZFN

<400> SEQUENCE: 11

Asp Arg Ser Asn Arg Ile Lys
1               5

<210> SEQ ID NO 12
<211> LENGTH: 7
<212> TYPE: PRT
<213> ORGANISM: Artificial
<220> FEATURE:
<223> OTHER INFORMATION: recognition region of glucocorticoid receptor-
      targeted ZFN

<400> SEQUENCE: 12

Gln Arg Ser His Arg Asn Thr
1               5

<210> SEQ ID NO 13
<211> LENGTH: 7
<212> TYPE: PRT
<213> ORGANISM: Artificial
<220> FEATURE:
<223> OTHER INFORMATION: recognition region of glucocorticoid receptor-
      targeted ZFN

<400> SEQUENCE: 13

Arg Ser Asp Ala Leu Thr Gln
1               5

<210> SEQ ID NO 14
<211> LENGTH: 7
<212> TYPE: PRT
<213> ORGANISM: Artificial
<220> FEATURE:
<223> OTHER INFORMATION: recognition region of glucocorticoid receptor-
      targeted ZFN

<400> SEQUENCE: 14

Arg Ser Asp Val Leu Ser Glu
1               5

<210> SEQ ID NO 15
<211> LENGTH: 7
<212> TYPE: PRT
<213> ORGANISM: Artificial
<220> FEATURE:
<223> OTHER INFORMATION: recognition region of glucocorticoid receptor-
      targeted ZFN

<400> SEQUENCE: 15
```

-continued

Asp Arg Ser Asn Leu Thr Arg
1               5

<210> SEQ ID NO 16
<211> LENGTH: 7
<212> TYPE: PRT
<213> ORGANISM: Artificial
<220> FEATURE:
<223> OTHER INFORMATION: recognition region of glucocorticoid receptor-
      targeted ZFN

<400> SEQUENCE: 16

Asp Ser Asp His Leu Thr Glu
1               5

<210> SEQ ID NO 17
<211> LENGTH: 7
<212> TYPE: PRT
<213> ORGANISM: Artificial
<220> FEATURE:
<223> OTHER INFORMATION: recognition region of glucocorticoid receptor-
      targeted ZFN

<400> SEQUENCE: 17

Asp Arg Ala Asn Leu Ser Arg
1               5

<210> SEQ ID NO 18
<211> LENGTH: 7
<212> TYPE: PRT
<213> ORGANISM: Artificial
<220> FEATURE:
<223> OTHER INFORMATION: recognition region of glucocorticoid receptor-
      targeted ZFN

<400> SEQUENCE: 18

Arg Ser Asp Asn Leu Ser Asn
1               5

<210> SEQ ID NO 19
<211> LENGTH: 7
<212> TYPE: PRT
<213> ORGANISM: Artificial
<220> FEATURE:
<223> OTHER INFORMATION: recognition region of glucocorticoid receptor-
      targeted ZFN

<400> SEQUENCE: 19

Thr Asn Ser Asn Arg Ile Lys
1               5

<210> SEQ ID NO 20
<211> LENGTH: 7
<212> TYPE: PRT
<213> ORGANISM: Artificial
<220> FEATURE:
<223> OTHER INFORMATION: recognition region of glucocorticoid receptor-
      targeted ZFN

<400> SEQUENCE: 20

Thr Ser Ser Asp Arg Lys Lys
1               5

<210> SEQ ID NO 21
<211> LENGTH: 7
<212> TYPE: PRT
<213> ORGANISM: Artificial

```
<220> FEATURE:
<223> OTHER INFORMATION: recognition region of glucocorticoid receptor-
      targeted ZFN

<400> SEQUENCE: 21

Arg Ser Asp Thr Leu Arg Cys
1               5

<210> SEQ ID NO 22
<211> LENGTH: 7
<212> TYPE: PRT
<213> ORGANISM: Artificial
<220> FEATURE:
<223> OTHER INFORMATION: recognition region of glucocorticoid receptor-
      targeted ZFN

<400> SEQUENCE: 22

Glu Arg Arg Ser Leu Arg Tyr
1               5

<210> SEQ ID NO 23
<211> LENGTH: 7
<212> TYPE: PRT
<213> ORGANISM: Artificial
<220> FEATURE:
<223> OTHER INFORMATION: recognition region of glucocorticoid receptor-
      targeted ZFN

<400> SEQUENCE: 23

Thr Ser Arg Ala Leu Thr Ala
1               5

<210> SEQ ID NO 24
<211> LENGTH: 7
<212> TYPE: PRT
<213> ORGANISM: Artificial
<220> FEATURE:
<223> OTHER INFORMATION: recognition region of glucocorticoid receptor-
      targeted ZFN

<400> SEQUENCE: 24

Arg Ser Asp Asn Leu Ser Glu
1               5

<210> SEQ ID NO 25
<211> LENGTH: 7
<212> TYPE: PRT
<213> ORGANISM: Artificial
<220> FEATURE:
<223> OTHER INFORMATION: recognition region of glucocorticoid receptor-
      targeted ZFN

<400> SEQUENCE: 25

Gln Asn Ala Asn Arg Lys Thr
1               5

<210> SEQ ID NO 26
<211> LENGTH: 7
<212> TYPE: PRT
<213> ORGANISM: Artificial
<220> FEATURE:
<223> OTHER INFORMATION: recognition region of glucocorticoid receptor-
      targeted ZFN

<400> SEQUENCE: 26

Glu Arg Ala Asn Arg Asn Ser
1               5
```

-continued

<210> SEQ ID NO 27
<211> LENGTH: 7
<212> TYPE: PRT
<213> ORGANISM: Artificial
<220> FEATURE:
<223> OTHER INFORMATION: recognition region of glucocorticoid receptor-
      targeted ZFN

<400> SEQUENCE: 27

Arg Ser Ala Asn Leu Thr Arg
1               5

<210> SEQ ID NO 28
<211> LENGTH: 7
<212> TYPE: PRT
<213> ORGANISM: Artificial
<220> FEATURE:
<223> OTHER INFORMATION: recognition region of glucocorticoid receptor-
      targeted ZFN

<400> SEQUENCE: 28

Arg Ser Asp Asn Leu Ser Thr
1               5

<210> SEQ ID NO 29
<211> LENGTH: 7
<212> TYPE: PRT
<213> ORGANISM: Artificial
<220> FEATURE:
<223> OTHER INFORMATION: recognition region of glucocorticoid receptor-
      targeted ZFN

<400> SEQUENCE: 29

His Ser His Ala Arg Ile Lys
1               5

<210> SEQ ID NO 30
<211> LENGTH: 7
<212> TYPE: PRT
<213> ORGANISM: Artificial
<220> FEATURE:
<223> OTHER INFORMATION: recognition region of glucocorticoid receptor-
      targeted ZFN

<400> SEQUENCE: 30

Thr Ser Gly Asn Leu Thr Arg
1               5

<210> SEQ ID NO 31
<211> LENGTH: 7
<212> TYPE: PRT
<213> ORGANISM: Artificial
<220> FEATURE:
<223> OTHER INFORMATION: recognition region of glucocorticoid receptor-
      targeted ZFN

<400> SEQUENCE: 31

Thr Ser Gly Ser Leu Thr Arg
1               5

<210> SEQ ID NO 32
<211> LENGTH: 7
<212> TYPE: PRT
<213> ORGANISM: Artificial
<220> FEATURE:
<223> OTHER INFORMATION: recognition region of glucocorticoid receptor-
      targeted ZFN

```
<400> SEQUENCE: 32

Asp Gly Trp Asn Arg Asp Cys
1               5

<210> SEQ ID NO 33
<211> LENGTH: 7
<212> TYPE: PRT
<213> ORGANISM: Artificial
<220> FEATURE:
<223> OTHER INFORMATION: recognition region of glucocorticoid receptor-
      targeted ZFN

<400> SEQUENCE: 33

Asp Ser Trp Asn Leu Gln Val
1               5

<210> SEQ ID NO 34
<211> LENGTH: 7
<212> TYPE: PRT
<213> ORGANISM: Artificial
<220> FEATURE:
<223> OTHER INFORMATION: recognition region of glucocorticoid receptor-
      targeted ZFN

<400> SEQUENCE: 34

Thr Asn Arg Asp Leu Asn Asp
1               5

<210> SEQ ID NO 35
<211> LENGTH: 7
<212> TYPE: PRT
<213> ORGANISM: Artificial
<220> FEATURE:
<223> OTHER INFORMATION: recognition region of glucocorticoid receptor-
      targeted ZFN

<400> SEQUENCE: 35

Asn Arg Lys Asn Leu Arg Gln
1               5

<210> SEQ ID NO 36
<211> LENGTH: 7
<212> TYPE: PRT
<213> ORGANISM: Artificial
<220> FEATURE:
<223> OTHER INFORMATION: recognition region of glucocorticoid receptor-
      targeted ZFN

<400> SEQUENCE: 36

Arg Ser Asp Ser Leu Ser Ala
1               5

<210> SEQ ID NO 37
<211> LENGTH: 7
<212> TYPE: PRT
<213> ORGANISM: Artificial
<220> FEATURE:
<223> OTHER INFORMATION: recognition region of glucocorticoid receptor-
      targeted ZFN

<400> SEQUENCE: 37

Arg Asn Asp Asn Arg Lys Thr
1               5

<210> SEQ ID NO 38
<211> LENGTH: 7
<212> TYPE: PRT
```

```
<213> ORGANISM: Artificial
<220> FEATURE:
<223> OTHER INFORMATION: recognition region of glucocorticoid receptor-
      targeted ZFN

<400> SEQUENCE: 38

Arg Ser Asp Asn Leu Ser Arg
1               5

<210> SEQ ID NO 39
<211> LENGTH: 7
<212> TYPE: PRT
<213> ORGANISM: Artificial
<220> FEATURE:
<223> OTHER INFORMATION: recognition region of glucocorticoid receptor-
      targeted ZFN

<400> SEQUENCE: 39

Thr Asn Gln Asn Arg Ile Thr
1               5

<210> SEQ ID NO 40
<211> LENGTH: 7
<212> TYPE: PRT
<213> ORGANISM: Artificial
<220> FEATURE:
<223> OTHER INFORMATION: recognition region of glucocorticoid receptor-
      targeted ZFN

<400> SEQUENCE: 40

Arg Gln Asp Cys Leu Ser Leu
1               5

<210> SEQ ID NO 41
<211> LENGTH: 7
<212> TYPE: PRT
<213> ORGANISM: Artificial
<220> FEATURE:
<223> OTHER INFORMATION: recognition region of glucocorticoid receptor-
      targeted ZFN

<400> SEQUENCE: 41

His Lys His Val Leu Asp Asn
1               5

<210> SEQ ID NO 42
<211> LENGTH: 7
<212> TYPE: PRT
<213> ORGANISM: Artificial
<220> FEATURE:
<223> OTHER INFORMATION: recognition region of glucocorticoid receptor-
      targeted ZFN

<400> SEQUENCE: 42

Arg Ser Ala Asn Leu Ala Arg
1               5

<210> SEQ ID NO 43
<211> LENGTH: 7
<212> TYPE: PRT
<213> ORGANISM: Artificial
<220> FEATURE:
<223> OTHER INFORMATION: recognition region of glucocorticoid receptor-
      targeted ZFN

<400> SEQUENCE: 43

Arg Ser Asp Asn Leu Arg Glu
1               5
```

-continued

<210> SEQ ID NO 44
<211> LENGTH: 7
<212> TYPE: PRT
<213> ORGANISM: Artificial
<220> FEATURE:
<223> OTHER INFORMATION: recognition region of glucocorticoid receptor-
      targeted ZFN

<400> SEQUENCE: 44

Gln Ser Ser Asn Leu Ala Arg
1               5

<210> SEQ ID NO 45
<211> LENGTH: 7
<212> TYPE: PRT
<213> ORGANISM: Artificial
<220> FEATURE:
<223> OTHER INFORMATION: recognition region of glucocorticoid receptor-
      targeted ZFN

<400> SEQUENCE: 45

Gln Ser Ala Asp Arg Thr Lys
1               5

<210> SEQ ID NO 46
<211> LENGTH: 196
<212> TYPE: PRT
<213> ORGANISM: Planomicrobium okeanokoites

<400> SEQUENCE: 46

Gln Leu Val Lys Ser Glu Leu Glu Glu Lys Lys Ser Glu Leu Arg His
1               5                   10                  15

Lys Leu Lys Tyr Val Pro His Glu Tyr Ile Glu Leu Ile Glu Ile Ala
            20                  25                  30

Arg Asn Ser Thr Gln Asp Arg Ile Leu Glu Met Lys Val Met Glu Phe
        35                  40                  45

Phe Met Lys Val Tyr Gly Tyr Arg Gly Lys His Leu Gly Gly Ser Arg
    50                  55                  60

Lys Pro Asp Gly Ala Ile Tyr Thr Val Gly Ser Pro Ile Asp Tyr Gly
65                  70                  75                  80

Val Ile Val Asp Thr Lys Ala Tyr Ser Gly Gly Tyr Asn Leu Pro Ile
                85                  90                  95

Gly Gln Ala Asp Glu Met Gln Arg Tyr Val Glu Glu Asn Gln Thr Arg
            100                 105                 110

Asn Lys His Ile Asn Pro Asn Glu Trp Trp Lys Val Tyr Pro Ser Ser
        115                 120                 125

Val Thr Glu Phe Lys Phe Leu Phe Val Ser Gly His Phe Lys Gly Asn
    130                 135                 140

Tyr Lys Ala Gln Leu Thr Arg Leu Asn His Ile Thr Asn Cys Asn Gly
145                 150                 155                 160

Ala Val Leu Ser Val Glu Glu Leu Leu Ile Gly Gly Glu Met Ile Lys
                165                 170                 175

Ala Gly Thr Leu Thr Leu Glu Glu Val Arg Arg Lys Phe Asn Asn Gly
            180                 185                 190

Glu Ile Asn Phe
            195

<210> SEQ ID NO 47
<211> LENGTH: 196

```
<212> TYPE: PRT
<213> ORGANISM: Artificial
<220> FEATURE:
<223> OTHER INFORMATION: engineered FokI cleavage half-domain with E490K
      and I538K mutations

<400> SEQUENCE: 47

Gln Leu Val Lys Ser Glu Leu Glu Glu Lys Lys Ser Glu Leu Arg His
1               5                   10                  15

Lys Leu Lys Tyr Val Pro His Glu Tyr Ile Glu Leu Ile Glu Ile Ala
            20                  25                  30

Arg Asn Ser Thr Gln Asp Arg Ile Leu Glu Met Lys Val Met Glu Phe
        35                  40                  45

Phe Met Lys Val Tyr Gly Tyr Arg Gly Lys His Leu Gly Gly Ser Arg
    50                  55                  60

Lys Pro Asp Gly Ala Ile Tyr Thr Val Gly Ser Pro Ile Asp Tyr Gly
65                  70                  75                  80

Val Ile Val Asp Thr Lys Ala Tyr Ser Gly Gly Tyr Asn Leu Pro Ile
                85                  90                  95

Gly Gln Ala Asp Glu Met Gln Arg Tyr Val Lys Glu Asn Gln Thr Arg
            100                 105                 110

Asn Lys His Ile Asn Pro Asn Glu Trp Trp Lys Val Tyr Pro Ser Ser
        115                 120                 125

Val Thr Glu Phe Lys Phe Leu Phe Val Ser Gly His Phe Lys Gly Asn
    130                 135                 140

Tyr Lys Ala Gln Leu Thr Arg Leu Asn His Lys Thr Asn Cys Asn Gly
145                 150                 155                 160

Ala Val Leu Ser Val Glu Glu Leu Leu Ile Gly Gly Glu Met Ile Lys
                165                 170                 175

Ala Gly Thr Leu Thr Leu Glu Glu Val Arg Arg Lys Phe Asn Asn Gly
            180                 185                 190

Glu Ile Asn Phe
        195

<210> SEQ ID NO 48
<211> LENGTH: 196
<212> TYPE: PRT
<213> ORGANISM: Artificial
<220> FEATURE:
<223> OTHER INFORMATION: engineered FokI cleavage half-domain with Q486E
      and I499L mutations

<400> SEQUENCE: 48

Gln Leu Val Lys Ser Glu Leu Glu Glu Lys Lys Ser Glu Leu Arg His
1               5                   10                  15

Lys Leu Lys Tyr Val Pro His Glu Tyr Ile Glu Leu Ile Glu Ile Ala
            20                  25                  30

Arg Asn Ser Thr Gln Asp Arg Ile Leu Glu Met Lys Val Met Glu Phe
        35                  40                  45

Phe Met Lys Val Tyr Gly Tyr Arg Gly Lys His Leu Gly Gly Ser Arg
    50                  55                  60

Lys Pro Asp Gly Ala Ile Tyr Thr Val Gly Ser Pro Ile Asp Tyr Gly
65                  70                  75                  80

Val Ile Val Asp Thr Lys Ala Tyr Ser Gly Gly Tyr Asn Leu Pro Ile
                85                  90                  95

Gly Gln Ala Asp Glu Met Glu Arg Tyr Val Glu Glu Asn Gln Thr Arg
            100                 105                 110
```

```
            Asn Lys His Leu Asn Pro Asn Glu Trp Trp Lys Val Tyr Pro Ser Ser
                    115                 120                 125

Val Thr Glu Phe Lys Phe Leu Phe Val Ser Gly His Phe Lys Gly Asn
                130                 135                 140

Tyr Lys Ala Gln Leu Thr Arg Leu Asn His Ile Thr Asn Cys Asn Gly
            145                 150                 155                 160

Ala Val Leu Ser Val Glu Glu Leu Leu Ile Gly Gly Glu Met Ile Lys
                            165                 170                 175

Ala Gly Thr Leu Thr Leu Glu Glu Val Arg Arg Lys Phe Asn Asn Gly
                            180                 185                 190

Glu Ile Asn Phe
                    195

<210> SEQ ID NO 49
<211> LENGTH: 30
<212> TYPE: DNA
<213> ORGANISM: Artificial
<220> FEATURE:
<223> OTHER INFORMATION: primer

<400> SEQUENCE: 49
tcataacact gttcttcccc ttctttagcc                                    30

<210> SEQ ID NO 50
<211> LENGTH: 28
<212> TYPE: DNA
<213> ORGANISM: Artificial
<220> FEATURE:
<223> OTHER INFORMATION: primer

<400> SEQUENCE: 50
tcaaaacaca cactacctto cactgctc                                      28

<210> SEQ ID NO 51
<211> LENGTH: 26
<212> TYPE: DNA
<213> ORGANISM: Artificial
<220> FEATURE:
<223> OTHER INFORMATION: primer

<400> SEQUENCE: 51
acacctggat gaccaaatga ccctac                                        26

<210> SEQ ID NO 52
<211> LENGTH: 32
<212> TYPE: DNA
<213> ORGANISM: Artificial
<220> FEATURE:
<223> OTHER INFORMATION: primer

<400> SEQUENCE: 52
cctagatacc tagtaggatt gtttcagtcc tg                                 32

<210> SEQ ID NO 53
<211> LENGTH: 14
<212> TYPE: DNA
<213> ORGANISM: Artificial
<220> FEATURE:
<223> OTHER INFORMATION: random sequence
<220> FEATURE:
<221> NAME/KEY: misc_feature
<222> LOCATION: (1)..(14)
<223> OTHER INFORMATION: n is a, c, g, or t

<400> SEQUENCE: 53
```

```
nnnnnnnnnn nnnn                                                      14

<210> SEQ ID NO 54
<211> LENGTH: 14
<212> TYPE: DNA
<213> ORGANISM: Artificial
<220> FEATURE:
<223> OTHER INFORMATION: randomized DNA sequence
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (9)..(11)
<223> OTHER INFORMATION: n is a, c, g, or t
<220> FEATURE:
<221> NAME/KEY: misc_feature
<222> LOCATION: (14)..(14)
<223> OTHER INFORMATION: n is a, c, g, or t

<400> SEQUENCE: 54
ngnnncggnn nagn                                                      14

<210> SEQ ID NO 55
<211> LENGTH: 14
<212> TYPE: DNA
<213> ORGANISM: Artificial
<220> FEATURE:
<223> OTHER INFORMATION: randomized DNA sequence

<400> SEQUENCE: 55
agacccggtc aagt                                                      14

<210> SEQ ID NO 56
<211> LENGTH: 14
<212> TYPE: DNA
<213> ORGANISM: Artificial
<220> FEATURE:
<223> OTHER INFORMATION: randomized DNA sequence

<400> SEQUENCE: 56
cgaaccggtt aagt                                                      14

<210> SEQ ID NO 57
<211> LENGTH: 14
<212> TYPE: DNA
<213> ORGANISM: Artificial
<220> FEATURE:
<223> OTHER INFORMATION: randomized DNA sequence

<400> SEQUENCE: 57
tgacacggtc cagc                                                      14
```

ISOLATED HUMAN CELL WITH AN INACTIVATED GLUCOCORTICOID RECEPTOR GENE

CROSS-REFERENCE TO RELATED APPLICATIONS

The present application is a continuation application of U.S. patent application Ser. No. 11/983,888, filed on Nov. 13, 2007, which claims the benefit of U.S. Provisional Application No. 60/859,025, filed Nov. 13, 2006; U.S. Provisional Application No. 60/859,417, filed Nov. 15, 2006 and U.S. Provisional Application No. 60/967,820, filed Sep. 7, 2007, all of which disclosures are hereby incorporated by reference in their entireties herein.

STATEMENT OF RIGHTS TO INVENTIONS MADE UNDER FEDERALLY SPONSORED RESEARCH

Not applicable.

TECHNICAL FIELD

The present disclosure is in the fields of immunology, immune system modulation and genome modification, including targeted mutagenesis, targeted genomic integration and targeted recombination.

BACKGROUND

The human glucocorticoid receptor (GR) is expressed in almost all cells of the body. Upon binding of glucocorticoid hormones such as cortisol the receptor is translocated to the cell nucleus and activates a tissue-specific set of target genes. The fact that GR target genes vary from one tissue to another results in a pleiotropic pattern of GR effects in different tissues.

Many of the physiological actions of glucocorticoid hormones are of medical interest and present potential areas for clinical intervention. For example, in Cushing's syndrome, excess GR activity leads to high blood pressure. In the brain, abnormalities in the GR pathway have been linked to depression and mood disorders; and, in the lung, such abnormalities have been associated with asthma and chronic airway diseases.

One of the best-characterized clinical activities of glucocorticoid hormones is their anti-inflammatory action, which is due to their immuno-suppressive effects. Exposure of T-cells to glucocorticoid hormones leads to T-cell anergy and interferes with T-cell activation. For a recent review, see Rhen, T. et al. (2005). *N. Engl. J. Med.* 353(16):1711-23. Long-term treatment with glucocorticoids leads to serious side effects like diabetes and osteoporosis. See discussion in Rosen, J. et al. (2005) *Endocr. Rev.* 26(3):452-64. Moreover, suppression of the entire immune system can lead to the reactivation of latent viruses (see Reinke, P. et al. (1999) *Transpl Infect Dis* 1(3):157-64) and interferes with immunotherapy approaches; e.g., the delivery of a beneficial subset of immune cells to patients.

Many of the problems associated with the GR overactivation that accompanies glucocorticoid treatment could be solved if a method was available which allows selective disruption of GR function in a subset of cells; e.g., a characterized population of T-cells. One such method would be to alter the sequence of the gene encoding the GR. Indeed, the ability to manipulate (i.e. edit) the DNA sequence at specific locations in the genome has been a major goal of human genome biology for some time. A variety of techniques have previously been tested for this purpose, but the frequencies of genome modification achieved with these methods have generally been too low for therapeutic applications. See, e.g., Yanez, R. J. et al. (1998) *Gene Ther.* 5(2): 149-159.

Another important application of genome editing is the insertion of clinically useful transgenes into the genome. However, a crucial requirement for any genome editing method is that it allow for targeted insertion into a defined location. The importance of the requirement for precisely targeted integration of a therapeutic transgene was underscored by the recent observation, in a clinical trial for treatment of X-linked SCID that the random integration of transgenes used for human gene therapy resulted, in certain cases, in insertional mutagenesis which led to oncogenic transformation of target cells. Hacein-Bey-Abina, S. et al. (2003). *Science* 302(5644):415-9.

Various methods and compositions for targeted cleavage of genomic DNA have been described. Such targeted cleavage events can be used, for example, to induce targeted mutagenesis, induce targeted deletions of cellular DNA sequences, and facilitate targeted recombination at a predetermined chromosomal locus. See, for example, United States patent application publications US 2003/0232410 (Dec. 18, 2003), US 2005/0026157 (Feb. 3, 2005), US 2005/0064474 (Mar. 24, 2005), US 2005/0208489 (Sep. 22, 2005) and US 2006/0188987 (Aug. 24, 2006); the disclosures of which are incorporated by reference in their entireties for all purposes. Targeted integration of exogenous sequences can also be accomplished. See U.S. patent application Ser. No. 11/493,423 (filed Jul. 26, 2006) the disclosure of which is incorporated by reference in its entirety for all purposes. See also PCT WO 2005/084190 (Sep. 15, 2005), the disclosure of which is incorporated by reference in its entirety for all purposes.

However, methods and compositions for specific cleavage of the human glucocorticoid receptor gene, and for modulation of immune function by modification of the GR gene, have not heretofore been described.

SUMMARY

Disclosed herein are methods and compositions for alteration of the nucleotide sequence of the human gene encoding the glucocorticoid receptor (GR). In certain embodiments, alteration of the sequence of the human GR gene inactivates GR function.

The methods include expression, in a cell, of a pair of zinc finger nucleases targeted to the human GR gene, which catalyze double stranded cleavage of sequences in the GR gene. Zinc finger nucleases are fusion proteins, comprising a zinc finger DNA-binding domain that has been engineered to bind to a target sequence and a cleavage half-domain. Expression of the zinc finger nucleases in a cell can be achieved by introduction of the nucleases themselves, RNA encoding the nucleases, or DNA encoding the nucleases, into the cell. GR-targeted zinc finger nucleases comprise zinc finger DNA-binding domains that have been engineered to bind to target sites in the GR gene. Engineering of a zinc finger DNA-binding domain includes determination of the amino acid sequence of the zinc fingers required for binding to the target nucleotide sequence (which may be achieved by computational or empirical means) and construction of a polynucleotide or polypeptide sequence corresponding to the desired amino acid sequence(s).

Exemplary engineered zinc finger DNA-binding domains targeted to the human GR gene are shown in Table 2 and their target sequences are shown in Table 1. Thus, this disclosure provides zinc finger nucleases targeted to any site in the human GR gene, and polynucleotides encoding said zinc finger nucleases. Cells comprising the aforementioned zinc finger nucleases and polynucleotides are also provided, for example, isolated cells, either primary cells or cells in culture.

In certain embodiments, targeted cleavage of the human GR gene by the zinc finger nucleases induces sequence alterations resulting from non-homologous end-joining (NHEJ). In additional embodiments, two zinc finger nucleases are expressed in a cell, and a donor polynucleotide is introduced into the cell. The donor polynucleotide contains a first region of homology to sequences upstream of the double-strand break created by the zinc finger nucleases, and a second region of homology to sequences downstream of the double-strand break. The donor polynucleotide optionally contains exogenous sequences that are non-homologous to the GR gene, which may comprise a transgene such as, for example, a chimeric T-cell receptor.

Inactivation of GR function by altering the primary nucleotide sequence of the GR gene, as described herein, can be used to prevent GR-mediated immune suppression in a variety of applications.

In one aspect, provided herein is a fusion protein comprising: (i) a zinc finger DNA-binding domain that has been engineered to bind a target sequence in the GR gene, and (ii) a cleavage half-domain. In certain embodiments, the zinc finger DNA-binding domain comprises a set of amino acid sequences in the order shown in a row of Table 2. Polynucleotides encoding any of the fusion proteins described herein are also provided.

In another aspect, the present disclosure provides a method for inactivating glucocorticoid receptor (GR) function in a cell, the method comprising: expressing in the cell a pair of fusion proteins, wherein each fusion protein comprises: (i) a zinc finger DNA-binding domain that has been engineered to bind a target sequence in the GR gene, and (ii) a cleavage half-domain; such that the fusion proteins catalyze a double-strand break in the GR gene. In certain embodiments, the zinc finger DNA-binding domain of a fusion protein comprises a set of amino acid sequences in the order shown in a row of Table 2. Any of the methods described herein may further comprise the step introducing a polynucleotide into the cell, wherein the polynucleotide comprises a first region of homology to sequences upstream of the double-strand break and a second region of homology to sequences downstream of the double-strand break. Optionally, the polynucleotide further comprises exogenous sequences (e.g., a transgene such as a modified receptor) that are non-homologous to the GR gene. Furthermore, any of the methods may prevent glucocorticoid-mediated immune suppression and/or T-cell anergy.

In yet another aspect, the disclosure provides methods of selecting cells into which an exogenous sequence has been introduced into a GR gene. The method comprises expressing ZFNs as described herein to cause a double-stranded break in a GR gene and introducing a donor polynucleotide (comprising GR homology arms and the exogenous sequence) into the cell. Cells in which the donor polynucleotide has been inserted into a GR gene are then selected for by growing the cells in the presence of a corticosteroid, which kills cells expressing normal amounts of GR. The term "corticosteriod" includes naturally occurring steroid hormones such as coritsol, corticosterone, cortisone and aldosterone. The term also includes synthetic drugs with corticosteroid-like effect including, for example, dexamethasone, prednisone, Fludrocortisone (Florinef®) and the like. In certain embodiments, the corticosteroid is dexamethasone. In any of these methods, the exogenous sequence may comprise a transgene (a sequence encoding a polypeptide of interest). Alternatively, the exogenous sequence may be a non-coding sequence.

In any of the methods described herein, the ZFNs are expressed using a viral delivery vector, for example, a replication-defective viral vector. In certain embodiments, the viral delivery vector is an adenovirus, a hybrid adenovirus or a non-integrating lentivirus.

Accordingly, the disclosure includes, but is not limited to, the following embodiments.

1. A method for inactivating glucocorticoid receptor (GR) function in a cell, the method comprising:
   expressing in the cell a pair of fusion proteins, wherein each fusion protein comprises:
   (i) a zinc finger DNA-binding domain that has been engineered to bind a target sequence in the GR gene, and
   (ii) a cleavage half-domain;
   such that the fusion proteins catalyze a double-strand break in the GR gene.

2. The method of 1, wherein the zinc finger DNA-binding domain of a fusion protein comprises a set of amino acid sequences in the order shown in a row of Table 2.

3. The method of 1, further comprising introducing a polynucleotide into the cell, wherein the polynucleotide comprises a first region of homology to sequences upstream of the double-strand break and a second region of homology to sequences downstream of the double-strand break.

4. The method of 3, wherein the polynucleotide further comprises exogenous sequences that are non-homologous to the GR gene.

5. The method of 4, wherein the exogenous sequences comprise a transgene.

6. The method of 5, wherein the transgene encodes a modified receptor.

7. The method of 1, wherein inactivation of GR function prevents glucocorticoid-mediated immune suppression.

8. The method of 1, wherein inactivation of GR function prevents T-cell anergy.

9. A fusion protein comprising:
   (i) a zinc finger DNA-binding domain that has been engineered to bind a target sequence in the GR gene, and
   (ii) a cleavage half-domain.

10. The fusion protein of 9, wherein the zinc finger DNA-binding domain comprises a set of amino acid sequences in the order shown in a row of Table 2.

11. A polynucleotide encoding the fusion protein of 9.

12. The method of 1, wherein the expressing step comprises contacting the cell with a viral delivery vector.

13. The method of 12, wherein the vector is replication-defective.

14. The method of 12, wherein the viral delivery vector is an adenovirus, a hybrid adenovirus or a non-integrating lentivirus.

15. A method of selecting cells comprising an exogenous sequence in a GR gene, the method comprising
   expressing a pair of fusion proteins in the cell, wherein each fusion protein comprises:
   (i) a zinc finger DNA-binding domain that has been engineered to bind a target sequence in a GR gene, and
   (ii) a cleavage half-domain;

such that the fusion proteins catalyze a double-strand break in the GR gene;

introducing a polynucleotide into the cell, wherein the polynucleotide comprises a first region of homology to sequences upstream of the double-strand break, a second region of homology to sequences downstream of the double-strand break and the exogenous sequence; and treating the cells with a natural or synthetic corticosteroid under conditions such that cells not comprising the exogenous sequence in a GR gene are killed, thereby selecting cells into which an exogenous sequence has been introduced into a GR gene.

16. The method of 15, wherein the corticosteroid is synthetic.

17. The method of 16, wherein the corticosteriod is dexamethasone.

18. The method of 15, wherein the exogenous sequence comprises a transgene.

19. The method of 15, wherein the expressing step comprises contacting the cell with a viral delivery vector.

20. The method of 19, wherein the vector is replication-defective.

21. The method of 19, wherein the viral delivery vector is an adenovirus, a hybrid adenovirus or a non-integrating lentivirus.

BRIEF DESCRIPTION OF THE DRAWINGS

FIG. 3A shows analysis of cleavage in Exon 3, and FIG. 3B shows analysis of cleavage in exon 6. An ethidium bromide stain of a 10% acrylamide gel is shown.

FIG. 4A shows PCR analysis of CEM14 cells transfected with GR-ZFNs and a zetakine-donor ZFN construct in the presence or absence of dexamethasone. Lanes with a "+" indicate cells treated with dexamethasone and lanes with a "−" indicate cells not treated with dexamethasone. "M" indicates the marker lane; "un" indicates untransfected cells; "zetakine" indicates cells transfected with the GR-ZFNs and the zetakine-donor construct; "p.c." indicates the positive control; and "n.c." indicates the negative control. FIG. 4B shows Southern blot analysis of CEM14 genomic DNA digested with SexA1. "M" indicates the marker lane; "un" indicates untransfected cells treated with dexamethasone; and "zetakine" indicates cells transfected with the GR-ZFNs and the zetakine-donor construct and treated with dexamethasone. Also shown with arrows are a 1.6 kb marker band; wild-type 5.2 kb band; and 2.0 kb band representing integrated zetakine transgene (TI).

FIG. 5 shows a chemiluminescent image of a protein blot that was probed with an antibody to the human glucocorticoid receptor. "CEM14" denotes untransfected cells; "ZFN" denotes CEM14 cells that had been transfected with a plasmid containing sequences encoding two ZFNs targeted to exon 3 of the GR gene, sequences containing a zetakine cassette, and sequences homologous to the GR gene. Bands corresponding to full-length and truncated GR protein are indicated to the left of the photograph.

FIGS. 7A and 7B, shows the results of Cel I assays demonstrating GR cleavage by ZFNs in CD-8$^+$ T-cells before (FIG. 7A) and after (FIG. 7B) treatment with dexamethasone. "ZFN-10" denotes cells infected with Ad5/F35 vector carrying ZFN pairs 9666 and 9674 at a multiplicity of infection (moi) of 10; "ZFN-30" denotes cells infected with Ad5/F35 vector carrying ZFN pairs 9666 and 9674 at moi of 30; "ZFN-100" denotes cells infected with Ad5/F35 vector carrying ZFN pairs 9666 and 9674 at moi of 100; and "GFP" denotes cells transfected with a control Ad5/F35 virus encoding green fluorescent protein at an moi of 100. Modification frequencies (percentages) are shown beneath various lanes.

FIG. 8 is a graph depicting glucocorticoid resistance of CD8+ cell pools described in Example 7, as determined by comparing cell viability before and after a second treatment with $10^{-4}$M dexamethasone for 8 days.

FIGS. 10A through 10D, are graphs depicting RT-PCR analysis of ZFN treated CD8+ T-cells for expression of the indicated genes. Panel A shows expression of IκBα; panel B shows expression of GILZ; panel C shows expression of MKP-1; and panel E shows expression of IFNγ. The samples tested are shown below the bars and were either untreated ("un") or treated with dexamethasone ("dex") for 20 hrs.

"Dex" refers to cells treated with $10^{-6}$ M dexamethasone. "U87MG" refers to cells cultured in the present of glioblastoma stimulator cells.

FIGS. 12A through 12E, are graphs depicting results of chromium release assays using control and GR-ZFN-treated CD8+ T-cells. The cells used are noted above each graph. Samples were obtained using the target cell lines indicated on the right at various effector:target ratios. The percentage of chromium release is plotted against the effector:target ratio for each data point.

Figure 13A:
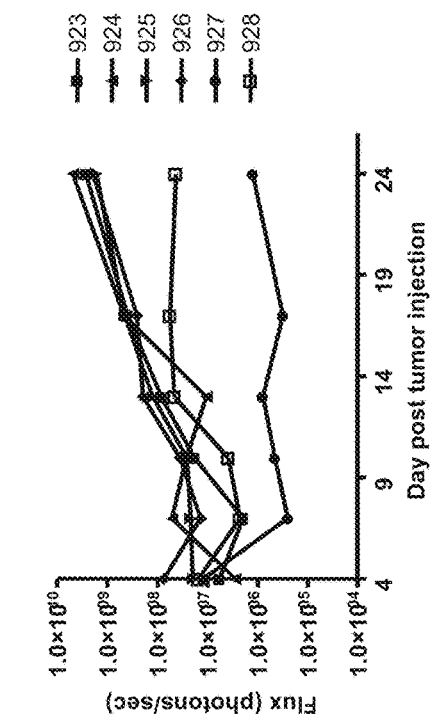
Figure 13B:
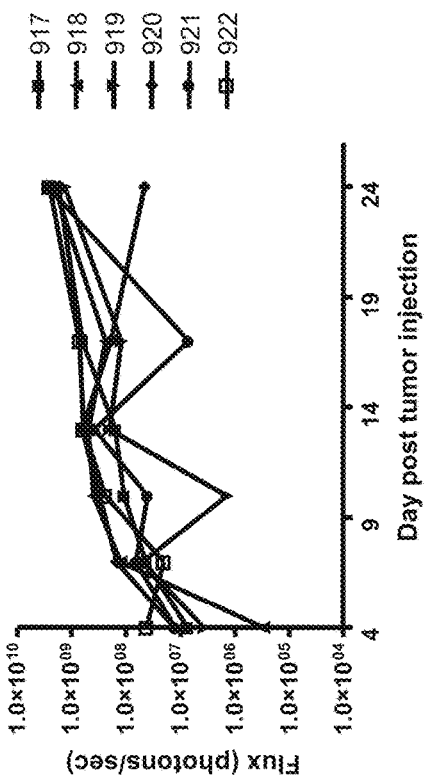
Figure 13C:
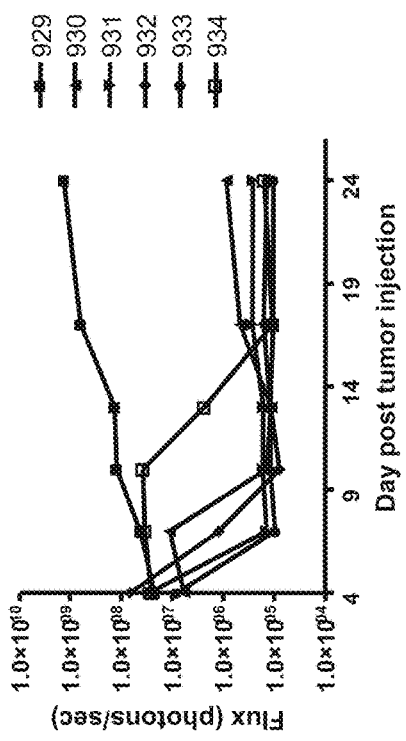

FIGS. 13A through 13C, are graphs depicting photons emitted from tumor cells in an orthotopic glioblastoma mouse model using luciferase labeled U87MG cells. Panel A shows photon emission from PBS control injections into the indicated animals. Panel B shows photon emission from animals injected with GFP100 controls. Panel C shows photon emission from animals injected with ZFN100 (GR-targeted ZFN at moi 100).

FIGS. 14A through 14D, are graphs depicting photons emitted from tumor cells in the orthotopic mouse glioblastoma model in the presence or absence of administered glucocorticoid hormone. FIGS. 14A and 14B show photon emission from PBS control injections in the absence (FIG. 14A) or presence (FIG. 14B) of dexamethasone. FIGS. 14C and 14D show photon emission from tumor cells of the mice following injecting of ZFN treated clone 10A1 into the tumor cells in the absence (FIG. 14C) or presence of dexamethasone (FIG. 14D).

FIG. 15 is a schematic depicting an experimental outline for determining the DNA-binding specificity of an individual zinc finger DNA-binding domain by SELEX. Hemaglutinin-tagged ZFNs were incubated with a pool of randomized DNA sequences in the presence of biotinylated anti-HA Fab antibody fragments. The tagged ZFN-DNA complexes were captured with streptavidin-coated magnetic beads, and the bound DNA was released and amplified by PCR. This process was repeated three times using the previous eluted, amplified pool of DNA as a starting sequence. After four iterations, the eluted DNA fragments were sequenced, and the consensus sequence was determined.

DETAILED DESCRIPTION

Disclosed herein are compositions and methods useful for altering the primary sequence of the gene encoding the glucocorticoid receptor (GR), utilizing fusion proteins comprising an engineered zinc finger DNA-binding domain and a cleavage domain (or cleavage half-domain), referred to herein as "zinc finger nucleases." Such sequence alterations can result in inactivation of human GR function. As is known in the art, zinc finger DNA-binding domains can be engineered, by selection methods or using techniques of rational design, to bind any target DNA sequence of choice. Fusion of engineered zinc finger DNA-binding domains to various types of functional domain, including transcriptional activation domains, transcriptional repression domains and nuclease domains, has also been described. See, for example, U.S. Pat. Nos. 6,534,261 and 6,933,113 and U.S. Patent Application Publication No. 2005-0064474; the disclosures of which are incorporated by reference in their entireties. Thus, by fusion of an engineered zinc finger binding domain to a nuclease domain, also known as a cleavage domain (i.e., a polypeptide domain with the ability to cleave double-stranded DNA), a custom endonuclease, having cleavage specificity for a sequence of choice, can be constructed. In certain embodiments, an engineered zinc finger DNA-binding domain is fused to a "cleavage half-domain" (i.e., a polypeptide domain which, when dimerized, possesses double-stranded DNA cleavage activity) and a pair of such fusion proteins is used for targeted DNA cleavage.

Cleavage of genomic DNA can result in the induction of a cellular repair mechanism known as non-homologous end joining (NHEJ). In the process of rejoining broken DNA ends, NHEJ often introduces mutations into the sequence at or around the site of the DNA break. The error-prone nature of the repair process, coupled with the ability of the zinc finger nuclease(s) to continue to bind and cleave their target sequence(s) until error-prone repair causes an alteration of the target sequence(s), results in the accumulation of mutations at or near the site of cleavage at a high frequency. Accordingly, targeted cleavage of endogenous genomic DNA sequences with zinc finger nucleases can be used to induce sequence changes (i.e., mutations) at or around the site of targeted cleavage. If such changes in nucleotide sequence occur in a region of the genome that encodes a protein, they usually result in alterations of the amino acid sequence of the encoded protein. For example, alteration of reading frame can result in production of a truncated protein due to premature translation termination. Alternatively, incorrect amino acids may be encoded. In either case, a non-functional polypeptide is produced. An additional consequence of sequence alteration following NHEJ is nonsense-mediated decay of mRNA encoded by the altered sequence. Thus, targeted DNA cleavage using zinc finger nucleases can be used to inactivate the function of a gene of choice. Inactivation can be achieved either by mutagenesis of both alleles or by mutagenesis of a single allele to generate a dominant negative mutant protein.

Targeted cleavage at a predetermined site in endogenous chromosomal DNA can also be used to facilitate integration of exogenous sequences at or near the site of cleavage, by both homology-directed and homology-independent mechanisms. For homology-dependent integration, a "donor sequence," containing sequences homologous to genomic sequences on both sides of the targeted cleavage site, is provided to cells in addition to the zinc finger nuclease(s). Such a donor sequence can also contain sequences that are nonhomologous to genomic sequences in the vicinity of the targeted cleavage site, optionally disposed between two stretches of homologous sequence. See, for example, United States Patent Application Publication No. 2005-0064474 (Mar. 24, 2005) and U.S. patent application Ser. No. 11/493,423 (Jul. 26, 2006), the disclosures of which are incorporated by reference in their entireties for all purposes. If integration of exogenous sequences occurs within the transcribed region of a gene, at both alleles, inactivation of the gene can result. Finally, targeted cleavage at two or more sites in endogenous chromosomal DNA can result in deletion of genomic sequences between the cleavage sites. See U.S. Patent Application Publication No. 2006-0188987 (Aug. 24, 2006), the disclosure of which is incorporated by reference in its entirety for all purposes. Thus, gene function can be inactivated by any of the foregoing mechanisms, all of which depend upon targeted cleavage of endogenous chromosomal DNA with one or more zinc finger nucleases.

The present disclosure provides methods and compositions for mutating the human glucocorticoid receptor (GR) gene. Such mutations can cause loss of GR function and result in modulation of immune function in a subject. In certain embodiments, mutation of the GR gene results from zinc finger nuclease-mediated integration of exogenous sequences into the human GR locus. In additional embodiments, the exogenous sequences comprise sequences encoding a modified receptor molecule.

The methods and compositions disclosed herein allow permanent abolition of glucocorticoid receptor function in a specified population of cells. This makes it possible, for example, to treat patients with immunosuppressant glucocorticoid hormones, while allowing those patients to retain a subset of immune cells able to effect specific immune responses.

Also provided are methods and compositions which facilitate the use of the GR locus as a defined integration site for therapeutic transgenes.

General

Practice of the methods, as well as preparation and use of the compositions disclosed herein employ, unless otherwise indicated, conventional techniques in molecular biology, biochemistry, chromatin structure analysis, computational chemistry, cell culture, recombinant DNA and related fields as are within the skill of the art. These techniques are fully explained in the literature. See, for example, Sambrook et al. MOLECULAR CLONING: A LABORATORY MANUAL, Cold Spring Harbor Laboratory Press, Second edition, 1989, Third edition, 2001; Ausubel et al., CURRENT PROTOCOLS IN MOLECULAR BIOLOGY, John Wiley & Sons, New York, 1987 and periodic updates; and the series METHODS IN ENZYMOLOGY, Academic Press, San Diego.

Definitions

The terms "nucleic acid," "polynucleotide," and "oligonucleotide" are used interchangeably and refer to a deoxyribonucleotide or ribonucleotide polymer, in linear or circular conformation, and in either single- or double-stranded form. For the purposes of the present disclosure, these terms are not to be construed as limiting with respect to the length of a polymer. The terms can encompass known analogues of natural nucleotides, as well as nucleotides that are modified in the base, sugar and/or phosphate moieties (e.g., phosphorothioate backbones). In general, an analogue of a particular nucleotide has the same base-pairing specificity; i.e., an analogue of A will base-pair with T.

The terms "polypeptide," "peptide" and "protein" are used interchangeably to refer to a polymer of amino acid residues. The term also applies to amino acid polymers in which one or more amino acids are chemical analogues or modified derivatives of a corresponding naturally-occurring amino acids.

"Binding" refers to a sequence-specific, non-covalent interaction between macromolecules (e.g., between a protein and a nucleic acid). Not all components of a binding interaction need be sequence-specific (e.g., contacts with phosphate residues in a DNA backbone), as long as the interaction as a whole is sequence-specific. Such interactions are generally characterized by a dissociation constant (Kd) of 10-6 M-1 or lower. "Affinity" refers to the strength of binding: increased binding affinity being correlated with a lower Kd.

A "binding protein" is a protein that is able to bind non-covalently to another molecule. A binding protein can bind to, for example, a DNA molecule (a DNA-binding protein), an RNA molecule (an RNA-binding protein) and/or a protein molecule (a protein-binding protein). In the case of a protein-binding protein, it can bind to itself (to form homodimers, homotrimers, etc.) and/or it can bind to one or more molecules of a different protein or proteins. A binding protein can have more than one type of binding activity. For example, zinc finger proteins have DNA-binding, RNA-binding and protein-binding activity.

A "zinc finger DNA binding protein" (or binding domain) is a protein, or a domain within a larger protein, that binds DNA in a sequence-specific manner through one or more zinc fingers, which are regions of amino acid sequence within the binding domain whose structure is stabilized through coordination of a zinc ion. The term zinc finger DNA binding protein is often abbreviated as zinc finger protein or ZFP.

Zinc finger binding domains can be "engineered" to bind to a predetermined nucleotide sequence. Non-limiting examples of methods for engineering zinc finger proteins are design and selection. A designed zinc finger protein is a protein not occurring in nature whose design/composition results principally from rational criteria. Rational criteria for design include application of substitution rules and computerized algorithms for processing information in a database storing information of existing ZFP designs and binding data. See, for example, U.S. Pat. Nos. 6,140,081; 6,453,242; and 6,534,261; see also WO 98/53058; WO 98/53059; WO 98/53060; WO 02/016536 and WO 03/016496.

A "selected" zinc finger protein is a protein not found in nature whose production results primarily from an empirical process such as phage display, interaction trap or hybrid selection. See e.g., U.S. Pat. Nos. 5,789,538; 5,925,523; 6,007,988; 6,013,453; 6,200,759; WO 95/19431; WO 96/06166; WO 98/53057; WO 98/54311; WO 00/27878; WO 01/60970 WO 01/88197 and WO 02/099084.

The term "sequence" refers to a nucleotide sequence of any length, which can be DNA or RNA; can be linear, circular or branched and can be either single-stranded or double stranded. The term "donor sequence" refers to a nucleotide sequence that is inserted into a genome. A donor sequence can be of any length, for example between 2 and 10,000 nucleotides in length (or any integer value therebetween or thereabove), preferably between about 100 and 1,000 nucleotides in length (or any integer therebetween), more preferably between about 200 and 500 nucleotides in length.

A "homologous, non-identical sequence" refers to a first sequence which shares a degree of sequence identity with a second sequence, but whose sequence is not identical to that of the second sequence. For example, a polynucleotide comprising the wild-type sequence of a mutant gene is homologous and non-identical to the sequence of the mutant gene. In certain embodiments, the degree of homology between the two sequences is sufficient to allow homologous recombination therebetween, utilizing normal cellular mechanisms. Two homologous non-identical sequences can be any length and their degree of non-homology can be as small as a single nucleotide (e.g., for correction of a genomic point mutation by targeted homologous recombination) or as large as 10 or more kilobases (e.g., for insertion of a gene at a predetermined ectopic site in a chromosome). Two polynucleotides comprising the homologous non-identical sequences need not be the same length. For example, an exogenous polynucleotide (i.e., donor polynucleotide) of between 20 and 10,000 nucleotides or nucleotide pairs can be used.

Techniques for determining nucleic acid and amino acid sequence identity are known in the art. Typically, such techniques include determining the nucleotide sequence of the mRNA for a gene and/or determining the amino acid sequence encoded thereby, and comparing these sequences to a second nucleotide or amino acid sequence. Genomic sequences can also be determined and compared in this fashion. In general, identity refers to an exact nucleotide-to-nucleotide or amino acid-to-amino acid correspondence of two polynucleotides or polypeptide sequences, respectively. Two or more sequences (polynucleotide or amino acid) can be compared by determining their percent identity. The percent identity of two sequences, whether nucleic acid or amino acid sequences, is the number of exact matches between two aligned sequences divided by the length of the shorter sequences and multiplied by 100. An approximate alignment for nucleic acid sequences is provided by the local homology algorithm of Smith and Waterman, Advances in Applied Mathematics 2:482-489 (1981). This algorithm can be applied to amino acid sequences by using the scoring matrix developed by Dayhoff, Atlas of Protein Sequences and Structure, M. O. Dayhoff ed., 5 suppl. 3:353-358, National Biomedical Research Foundation, Washington, D.C., USA, and normalized by Gribskov, Nucl. Acids Res. 14(6):6745-6763 (1986). An exemplary implementation of this algorithm to determine percent identity of a sequence is provided by the Genetics Computer Group (Madison, Wis.) in the "BestFit" utility application. The default parameters for this method are described in the Wisconsin Sequence Analysis Package Program Manual, Version 8 (1995) (available from Genetics Computer Group, Madison, Wis.). A preferred method of establishing percent identity in the context of the present disclosure is to use the MPSRCH package of programs copyrighted by the University of Edinburgh, developed by John F. Collins and Shane S. Sturrok, and distributed by IntelliGenetics, Inc. (Mountain View, Calif.). From this suite of packages the Smith-Waterman algorithm can be employed where default parameters are used for the scoring table (for example, gap open penalty of 12, gap extension penalty of one, and a gap of six). From the data generated the "Match" value reflects sequence identity. Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR. Details of these programs can be found at the following internet address: http://www.ncbi.nlm.gov/cgi-bin/BLAST. With respect to sequences described herein, the range of desired degrees of sequence identity is approximately 80% to 100% and any integer value therebetween. Typically the percent identities between sequences are at least 70-75%, preferably 80-82%, more preferably 85-90%, even more preferably 92%, still more preferably 95%, and most preferably 98% sequence identity.

Alternatively, the degree of sequence similarity between polynucleotides can be determined by hybridization of polynucleotides under conditions that allow formation of stable duplexes between homologous regions, followed by digestion with single-stranded-specific nuclease(s), and size determination of the digested fragments. Two nucleic acid, or two polypeptide sequences are substantially homologous to each other when the sequences exhibit at least about 70%-75%, preferably 80%-82%, more preferably 85%-90%, even more preferably 92%, still more preferably 95%, and most preferably 98% sequence identity over a defined length of the molecules, as determined using the methods above. As used herein, substantially homologous also refers to sequences showing complete identity to a specified DNA or polypeptide sequence. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; Nucleic Acid Hybridization: A Practical Approach, editors B. D. Hames and S. J. Higgins, (1985) Oxford; Washington, D.C.; IRL Press).

Selective hybridization of two nucleic acid fragments can be determined as follows. The degree of sequence identity between two nucleic acid molecules affects the efficiency and strength of hybridization events between such molecules. A partially identical nucleic acid sequence will at least partially inhibit the hybridization of a completely identical sequence to a target molecule Inhibition of hybridization of the completely identical sequence can be assessed using hybridization assays that are well known in the art (e.g., Southern (DNA) blot, Northern (RNA) blot, solution hybridization, or the like, see Sambrook, et al., Molecular Cloning: A Laboratory Manual, Second Edition, (1989) Cold Spring Harbor, N.Y.). Such assays can be conducted using varying degrees of selectivity, for example, using conditions varying from low to high stringency. If conditions of low stringency are employed, the absence of non-specific binding can be assessed using a secondary probe that lacks even a partial degree of sequence identity (for example, a probe having less than about 30% sequence identity with the target molecule), such that, in the absence of non-specific binding events, the secondary probe will not hybridize to the target.

When utilizing a hybridization-based detection system, a nucleic acid probe is chosen that is complementary to a reference nucleic acid sequence, and then by selection of appropriate conditions the probe and the reference sequence selectively hybridize, or bind, to each other to form a duplex molecule. A nucleic acid molecule that is capable of hybridizing selectively to a reference sequence under moderately stringent hybridization conditions typically hybridizes under conditions that allow detection of a target nucleic acid sequence of at least about 10-14 nucleotides in length having at least approximately 70% sequence identity with the sequence of the selected nucleic acid probe. Stringent hybridization conditions typically allow detection of target nucleic acid sequences of at least about 10-14 nucleotides in length having a sequence identity of greater than about 90-95% with the sequence of the selected nucleic acid probe. Hybridization conditions useful for probe/reference sequence hybridization, where the probe and reference sequence have a specific degree of sequence identity, can be determined as is known in the art (see, for example, Nucleic Acid Hybridization: A Practical Approach, editors B. D. Hames and S. J. Higgins, (1985) Oxford; Washington, D.C.; IRL Press).

Conditions for hybridization are well-known to those of skill in the art. Hybridization stringency refers to the degree to which hybridization conditions disfavor the formation of hybrids containing mismatched nucleotides, with higher stringency correlated with a lower tolerance for mismatched hybrids. Factors that affect the stringency of hybridization are well-known to those of skill in the art and include, but are not limited to, temperature, pH, ionic strength, and concentration of organic solvents such as, for example, formamide and dimethylsulfoxide. As is known to those of skill in the art, hybridization stringency is increased by higher temperatures, lower ionic strength and lower solvent concentrations.

With respect to stringency conditions for hybridization, it is well known in the art that numerous equivalent conditions can be employed to establish a particular stringency by varying, for example, the following factors: the length and nature of the sequences, base composition of the various sequences, concentrations of salts and other hybridization solution components, the presence or absence of blocking agents in the hybridization solutions (e.g., dextran sulfate, and polyethylene glycol), hybridization reaction temperature and time parameters, as well as, varying wash conditions. The selection of a particular set of hybridization conditions is selected following standard methods in the art (see, for example, Sambrook, et al., Molecular Cloning: A Laboratory Manual, Second Edition, (1989) Cold Spring Harbor, N.Y.).

"Recombination" refers to a process of exchange of genetic information between two polynucleotides. For the purposes of this disclosure, "homologous recombination (HR)" refers to the specialized form of such exchange that takes place, for example, during repair of double-strand breaks in cells. This process requires nucleotide sequence homology, uses a "donor" molecule to template repair of a "target" molecule (i.e., the one that experienced the double-strand break), and is variously known as "non-crossover gene conversion" or "short tract gene conversion," because it leads to the transfer of genetic information from the donor to the target. Without wishing to be bound by any particular theory, such transfer can involve mismatch correction of heteroduplex DNA that forms between the broken target and the donor, and/or "synthesis-dependent strand annealing," in which the donor is used to resynthesize genetic information that will become part of the target, and/or related processes. Such specialized HR often results in an alteration of the sequence of the target molecule such that part or all of the sequence of the donor polynucleotide is incorporated into the target polynucleotide.

"Cleavage" refers to the breakage of the covalent backbone of a DNA molecule. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. DNA cleavage can result in the production of either blunt ends or staggered ends. In certain embodiments, fusion polypeptides are used for targeted double-stranded DNA cleavage.

A "cleavage domain" comprises one or more polypeptide sequences which possesses catalytic activity for DNA cleavage. A cleavage domain can be contained in a single polypeptide chain or cleavage activity can result from the association of two (or more) polypeptides. A "cleavage half-domain" is a polypeptide sequence which, in conjunction with a second polypeptide (either identical or different) forms a complex having cleavage activity (preferably double-strand cleavage activity). The terms "first and second cleavage half-domains;" "+ and − cleavage half-domains" and "right and left cleavage half-domains" are used interchangeably to refer to pairs of cleavage half-domains that dimerize.

An "engineered cleavage half-domain" is a cleavage half-domain that has been modified so as to form obligate heterodimers with another cleavage half-domain (e.g., another engineered cleavage half-domain). See, also, U.S. Patent Publication Nos. 20050064474 and 20060188987 and U.S. Provisional Application No. 60/808,486 (filed May 25, 2006), incorporated herein by reference in their entireties.

"Chromatin" is the nucleoprotein structure comprising the cellular genome. Cellular chromatin comprises nucleic acid, primarily DNA, and protein, including histones and non-histone chromosomal proteins. The majority of eukaryotic cellular chromatin exists in the form of nucleosomes, wherein a nucleosome core comprises approximately 150 base pairs of DNA associated with an octamer comprising two each of histones H2A, H2B, H3 and H4; and linker DNA (of variable length depending on the organism) extends between nucleosome cores. A molecule of histone H1 is generally associated with the linker DNA. For the purposes of the present disclosure, the term "chromatin" is meant to encompass all types of cellular nucleoprotein, both prokaryotic and eukaryotic. Cellular chromatin includes both chromosomal and episomal chromatin.

A "chromosome," is a chromatin complex comprising all or a portion of the genome of a cell. The genome of a cell is often characterized by its karyotype, which is the collection of all the chromosomes that comprise the genome of the cell. The genome of a cell can comprise one or more chromosomes.

An "episome" is a replicating nucleic acid, nucleoprotein complex or other structure comprising a nucleic acid that is not part of the chromosomal karyotype of a cell. Examples of episomes include plasmids and certain viral genomes.

An "accessible region" is a site in cellular chromatin in which a target site present in the nucleic acid can be bound by an exogenous molecule which recognizes the target site. Without wishing to be bound by any particular theory, it is believed that an accessible region is one that is not packaged into a nucleosomal structure. The distinct structure of an accessible region can often be detected by its sensitivity to chemical and enzymatic probes, for example, nucleases.

A "target site" or "target sequence" is a nucleic acid sequence that defines a portion of a nucleic acid to which a binding molecule will bind, provided sufficient conditions for binding exist. For example, the sequence 5' GAATTC 3' is a target site for the Eco RI restriction endonuclease.

An "exogenous" molecule is a molecule that is not normally present in a cell, but can be introduced into a cell by one or more genetic, biochemical or other methods. "Normal presence in the cell" is determined with respect to the particular developmental stage and environmental conditions of the cell. Thus, for example, a molecule that is present only during embryonic development of muscle is an exogenous molecule with respect to an adult muscle cell. Similarly, a molecule induced by heat shock is an exogenous molecule with respect to a non-heat-shocked cell. An exogenous molecule can comprise, for example, a functioning version of a malfunctioning endogenous molecule or a malfunctioning version of a normally-functioning endogenous molecule.

An exogenous molecule can be, among other things, a small molecule, such as is generated by a combinatorial chemistry process, or a macromolecule such as a protein, nucleic acid, carbohydrate, lipid, glycoprotein, lipoprotein, polysaccharide, any modified derivative of the above molecules, or any complex comprising one or more of the above molecules. Nucleic acids include DNA and RNA, can be single- or double-stranded; can be linear, branched or circular; and can be of any length. Nucleic acids include those capable of forming duplexes, as well as triplex-forming nucleic acids. See, for example, U.S. Pat. Nos. 5,176,996 and 5,422,251. Proteins include, but are not limited to, DNA-binding proteins, transcription factors, chromatin remodeling factors, methylated DNA binding proteins, polymerases, methylases, demethylases, acetylases, deacetylases, kinases, phosphatases, integrases, recombinases, ligases, topoisomerases, gyrases and helicases.

An exogenous molecule can be the same type of molecule as an endogenous molecule, e.g., an exogenous protein or nucleic acid. For example, an exogenous nucleic acid can comprise an infecting viral genome, a plasmid or episome introduced into a cell, or a chromosome that is not normally present in the cell. Methods for the introduction of exogenous molecules into cells are known to those of skill in the art and include, but are not limited to, lipid-mediated transfer (i.e., liposomes, including neutral and cationic lipids), electroporation, direct injection, cell fusion, particle bombardment, calcium phosphate co-precipitation, DEAE-dextran-mediated transfer and viral vector-mediated transfer.

By contrast, an "endogenous" molecule is one that is normally present in a particular cell at a particular developmental stage under particular environmental conditions. For example, an endogenous nucleic acid can comprise a chromosome, the genome of a mitochondrion, chloroplast or other organelle, or a naturally-occurring episomal nucleic acid. Additional endogenous molecules can include proteins, for example, transcription factors and enzymes.

A "fusion" molecule is a molecule in which two or more subunit molecules are linked, preferably covalently. The subunit molecules can be the same chemical type of molecule, or can be different chemical types of molecules. Examples of the first type of fusion molecule include, but are not limited to, fusion proteins (for example, a fusion between a ZFP DNA-binding domain and a cleavage domain) and fusion nucleic acids (for example, a nucleic acid encoding the fusion protein described supra). Examples of the second type of fusion molecule include, but are not limited to, a fusion between a triplex-forming nucleic acid and a polypeptide, and a fusion between a minor groove binder and a nucleic acid.

Expression of a fusion protein in a cell can result from delivery of the fusion protein to the cell or by delivery of a polynucleotide encoding the fusion protein to a cell, wherein the polynucleotide is transcribed, and the transcript is translated, to generate the fusion protein. Trans-splicing, polypeptide cleavage and polypeptide ligation can also be involved in expression of a protein in a cell. Methods for polynucleotide and polypeptide delivery to cells are presented elsewhere in this disclosure.

A "gene," for the purposes of the present disclosure, includes a DNA region encoding a gene product (see infra), as well as all DNA regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions.

"Gene expression" refers to the conversion of the information, contained in a gene, into a gene product. A gene product can be the direct transcriptional product of a gene (e.g., mRNA, tRNA, rRNA, antisense RNA, ribozyme, structural RNA or any other type of RNA) or a protein produced by translation of a mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation.

"Modulation" of gene expression refers to a change in the activity of a gene. Modulation of expression can include, but is not limited to, gene activation and gene repression.

"Eucaryotic" cells include, but are not limited to, fungal cells (such as yeast), plant cells, animal cells, mammalian cells and human cells (e.g., T-cells).

A "region of interest" is any region of cellular chromatin, such as, for example, a gene or a non-coding sequence within or adjacent to a gene, in which it is desirable to bind an exogenous molecule. Binding can be for the purposes of targeted DNA cleavage and/or targeted recombination. A region of interest can be present in a chromosome, an episome, an organellar genome (e.g., mitochondrial, chloroplast), or an infecting viral genome, for example. A region of interest can be within the coding region of a gene, within transcribed non-coding regions such as, for example, leader sequences, trailer sequences or introns, or within non-transcribed regions, either upstream or downstream of the coding region. A region of interest can be as small as a single nucleotide pair or up to 2,000 nucleotide pairs in length, or any integral value of nucleotide pairs.

The terms "operative linkage" and "operatively linked" (or "operably linked") are used interchangeably with reference to a juxtaposition of two or more components (such as sequence elements), in which the components are arranged such that both components function normally and allow the possibility that at least one of the components can mediate a function that is exerted upon at least one of the other components. By way of illustration, a transcriptional regulatory sequence, such as a promoter, is operatively linked to a coding sequence if the transcriptional regulatory sequence controls the level of transcription of the coding sequence in response to the presence or absence of one or more transcriptional regulatory factors. A transcriptional regulatory sequence is generally operatively linked in cis with a coding sequence, but need not be directly adjacent to it. For example, an enhancer is a transcriptional regulatory sequence that is operatively linked to a coding sequence, even though they are not contiguous.

With respect to fusion polypeptides, the term "operatively linked" can refer to the fact that each of the components performs the same function in linkage to the other component as it would if it were not so linked. For example, with respect to a fusion polypeptide in which a ZFP DNA-binding domain is fused to a cleavage domain, the ZFP DNA-binding domain and the cleavage domain are in operative linkage if, in the fusion polypeptide, the ZFP DNA-binding domain portion is able to bind its target site and/or its binding site, while the cleavage domain is able to cleave DNA in the vicinity of the target site.

A "functional fragment" of a protein, polypeptide or nucleic acid is a protein, polypeptide or nucleic acid whose sequence is not identical to the full-length protein, polypeptide or nucleic acid, yet retains the same function as the full-length protein, polypeptide or nucleic acid. A functional fragment can possess more, fewer, or the same number of residues as the corresponding native molecule, and/or can contain one ore more amino acid or nucleotide substitutions. Methods for determining the function of a nucleic acid (e.g., coding function, ability to hybridize to another nucleic acid) are well-known in the art. Similarly, methods for determining protein function are well-known. For example, the DNA-binding function of a polypeptide can be determined, for example, by filter-binding, electrophoretic mobility-shift, or immunoprecipitation assays. DNA cleavage can be assayed by gel electrophoresis. See Ausubel et al., supra. The ability of a protein to interact with another protein can be determined, for example, by co-immunoprecipitation, two-hybrid assays or complementation, both genetic and biochemical. See, for example, Fields et al. (1989) *Nature* 340:245-246; U.S. Pat. No. 5,585,245 and PCT WO 98/44350.

Design of Zinc Finger DNA-Binding Domains

Construction of zinc finger nucleases is described, for example, in U.S. Patent Application Publications 2003-0232410, 2005-0026157, 2005-0064474 and 2005-0208489, the disclosures of which are incorporated by reference in their entireties. Briefly, a non-naturally-occurring zinc finger DNA-binding domain, comprising 2, 3, 4, 5, 6 or more zinc fingers, is engineered to bind to a predetermined target nucleotide sequence. The engineered zinc finger binding domain is fused to a nuclease domain, a cleavage domain or a cleavage half-domain to form a zinc finger nuclease capable of DNA cleavage at or near the target nucleotide sequence. In certain embodiments, following conceptual design of the zinc finger DNA-binding domain, a polynucleotide encoding the zinc finger nuclease is constructed, using standard molecular biological methods.

Zinc finger nucleases, for facilitating mutagenesis of the human glucocorticoid receptor gene, are designed and synthesized as follows. The nucleotide sequences of relevant portions of the human glucocorticoid receptor gene are obtained. The sequences thus obtained are scanned, optionally using a computer program containing a listing of individual zinc fingers and their target sites and/or a listing of two-finger modules and their target sites, for a pair of target sequences, separated by 5-6 nucleotide pairs, wherein each target sequence can be bound by a 3-, 4-, 5- or 6-finger zinc finger protein. See, for example, U.S. Pat. No. 6,785,613; WO 98/53057; WO 01/53480 and U.S. Patent Application Publication No. 2003/0092000. Additional methods for ZFP design are disclosed, for example, in U.S. Pat. Nos. 5,789,538; 6,013,453; 6,410,248; 6,733,970; 6,746,838; 6,785,613; 6,866,997; 7,030,215; WO 01/088197; WO 02/099084; and US Patent Application Publications 2003/0044957; 2003/0108880; 2003/0134318 and 2004/0128717.

For each target sequence identified in the previous step, a gene encoding a fusion between a FokI cleavage half-domain and a zinc finger protein that binds to the target sequence is synthesized. See, for example, U.S. Pat. No. 5,436,150 and WO 2005/084190 and U.S. Patent Application Publication No. 2005/0064474. Each fusion protein can be tested for the affinity with which it binds to its target sequence, using an ELISA assay as described, for example, by Bartsevich et al. (2003) *Stem Cells* 21:632-637. Proteins having target sequence binding affinities which exceed a predetermined threshold value can subjected to further testing in a cell-based reporter assay.

Optionally, the binding specificity of one or more fusion proteins as described above can be assessed and, if necessary, improved, by alteration (including randomization) of one or more amino acid residues followed by a phage display assay against the target sequence (see, for example, WO 96/06166), and/or by methods of iterative optimization described in U.S. Pat. No. 6,794,136.

Cell-based testing is conducted as described, for example, in Urnov et al. (2005) *Nature* 435:646-651 and U.S. Patent Application Publication No. 2005/0064474. Briefly, a target sequence pair, identified as described above, is inserted into a defective chromosomal green fluorescent protein (GFP) gene, under the transcriptional control of a doxycycline-inducible promoter, in an appropriate cell line. Cells are transfected with nucleic acids encoding two zinc finger/FokI fusion proteins (each of which binds to one of the target sequences) and with a nucleic acid containing sequences that, if they serve as template for homology-directed repair of the defective chromosomal GFP gene, will reconstitute a functional GFP gene. Cells in which homology-directed repair has occurred can be identified and quantitated by fluorescence-activated cell sorting, following induction with doxycycline.

Zinc Finger Binding Domains Targeted to the Human Glucocorticoid Receptor Gene

Methods for inactivation of GR disclosed herein utilize zinc finger nucleases, comprising (1) a zinc finger DNA-binding domain which has been engineered to bind a target sequence of choice and (2) a cleavage domain or cleavage half-domain. Any such zinc finger nuclease having a target site in a human GR gene can be used in the disclosed methods. Alternatively, any pair of zinc finger nucleases, each comprising a cleavage half-domain, whose target sequences are separated by the appropriate number of nucleotides, can also be used. See, for example, U.S. Patent Application Publication No. 2005-0064474; Smith et al. (2000) *Nucleic Acids Res.* 28:3361-3369 and Bibikova et al. (2001) *Mol. Cell. Biol.* 21:289-297.

Exemplary zinc finger binding domains having target sites in the human GR gene are disclosed in Tables 1 and 2. Table 1 provides the target sequences of the exemplary binding domains and the location of those target sites in the GR gene. Table 2 shows the amino acid sequences of the engineered recognition regions (responsible for DNA-binding specificity) of these binding domains. Zinc finger sequences are shown in amino-to-carboxy order, with F1 denoting the zinc finger nearest the amino terminus of the protein.

TABLE 1

Target Sequences for GR-Targeted ZFNs

| Name[1] | Target Sequence[2] | Location[3] |
|---|---|---|
| 8718, 9967 | GACCTGtTGATAG (SEQ ID NO: 1) | nt 778-790 sense (exon 2) |
| 8893 | GACCTGtTGATAGATG (SEQ ID NO: 2) | nt 778-793 sense (exon 2) |
| 8719, 10415, 10404 | TCCAAGGACTCT (SEQ ID NO: 3) | nt 761-772 antisense (exon 2) |
| 8667, 9666 | CAACAGGACCAC (SEQ ID NO: 4) | nt 1370-1381 sense (exon 3) |

TABLE 1-continued

Target Sequences for GR-Targeted ZFNs

| Name[1] | Target Sequence[2] | Location[3] |
|---|---|---|
| 8668, 8669, 9671, 9674, 10201, 10205 | GTTGAGGAGCTG (SEQ ID NO: 5) | nt 1353-1364 antisense (exon 3) |
| 8531, 9737, 9846 | AATGAGTAAGTTG (SEQ ID NO: 6) | nt 2020-2023 sense (exon 6) + first 9 nt in intron 6 |
| 8653 | TCAGATCAGGAG (SEQ ID NO: 7) | nt 2003-2014 antisense (exon 6) |

[1] Each zinc finger binding domain is represented by a four- or five-digit number. Relevant amino acid sequences of these binding domains are shown in Table 2.
[2] Nucleotides in uppercase represent those present in target subsites bound by individual zinc fingers; nucleotides indicated in lowercase are not present in a subsite. See U.S. Pat. No. 6,453,242 and U.S. Patent Application Publication No. 2005-0064474 (both incorporated by reference) for a description of target subsites.
[3] Locations in the human glucocorticoid receptor locus are given with respect to the published sequence of the GRα mRNA. Hollenberg, S. M. et al. (1985). Nature 318(6047): 635-41; GenBank accession number X03225.

TABLE 2

Amino Acid Sequences of Recognition Regions of GR-Targeted ZFNs

| Name | F1 | F2 | F3 | F4 | F5 |
|---|---|---|---|---|---|
| Exon 2 | | | | | |
| 8718 | RSDYLST (SEQ ID NO: 8) | QNAHRKT (SEQ ID NO: 9) | RSDVLSA (SEQ ID NO: 10) | DRSNRIK (SEQ ID NO: 11) | |
| 9967 | RSDYLST (SEQ ID NO: 8) | QRSHRNT (SEQ ID NO: 12) | RSDVLSA (SEQ ID NO: 10) | DRSNRIK (SEQ ID NO: 11) | |
| 8893 | RSDALTQ (SEQ ID NO: 13) | RSDYLST (SEQ ID NO: 8) | QNAHRKT (SEQ ID NO: 9) | RSDVLSE (SEQ ID NO: 14) | DRSNLTR (SEQ ID NO: 15) |
| 8719 | DSDHLTE (SEQ ID NO: 16) | DRANLSR (SEQ ID NO: 17) | RSDNLSN (SEQ ID NO: 18) | TNSNRIK (SEQ ID NO: 19) | |
| 10404 | TSSDRKK (SEQ ID NO: 20) | DRANLSR (SEQ ID NO: 17) | RSDTLRC (SEQ ID NO: 21) | TNSNRIK (SEQ ID NO: 19) | |
| 10415 | TSSDRKK (SEQ ID NO: 20) | DRANLSR (SEQ ID NO: 17) | RSDNLSN (SEQ ID NO: 18) | ERRSLRY (SEQ ID NO: 22) | |
| Exon 3 | | | | | |
| 8667 | TSRALTA (SEQ ID NO: 23) | DRANLSR (SEQ ID NO: 17) | RSDNLSE (SEQ ID NO: 24) | QNANRKT (SEQ ID NO: 25) | |
| 9666 | TSRALTA (SEQ ID NO: 23) | DRANLSR (SEQ ID NO: 17) | RSDNLSE (SEQ ID NO: 24) | ERANRNS (SEQ ID NO: 26) | |
| 8668 | RSDVLSE (SEQ ID NO: 14) | RSANLTR (SEQ ID NO: 27) | RSDNLST (SEQ ID NO: 28) | HSHARIK (SEQ ID NO: 29) | |

| Name | F1 | F2 | F3 | F4 |
|---|---|---|---|---|
| 8669 | RSDVLSE (SEQ ID NO: 14) | RSANLTR (SEQ ID NO: 27) | TSGNLTR (SEQ ID NO: 30) | TSGSLTR (SEQ ID NO: 31) |
| 9671 | DGWNRDC (SEQ ID NO: 32) | RSANLTR (SEQ ID NO: 27) | TSGNLTR (SEQ ID NO: 30) | TSGSLTR (SEQ ID NO: 31) |
| 9674 | DSWNLQV (SEQ ID NO: 33) | RSANLTR (SEQ ID NO: 27) | TSGNLTR (SEQ ID NO: 30) | TSGSLTR (SEQ ID NO: 31) |
| 10201 | TNRDLND (SEQ ID NO: 34) | DRANLSR (SEQ ID NO: 17) | RSDNLSE (SEQ ID NO: 24) | ERANRNS (SEQ ID NO: 26) |
| 10205 | NRKNLRQ (SEQ ID NO: 35) | DRANLSR (SEQ ID NO: 17) | RSDNLSE (SEQ ID NO: 24) | ERANRNS (SEQ ID NO: 26) |

TABLE 2-continued

Amino Acid Sequences of Recognition Regions of GR-Targeted ZFNs

| | | | | |
|---|---|---|---|---|
| Exon 6 | | | | |
| 8531 | RSDSLSA (SEQ ID NO: 36) | RNDNRKT (SEQ ID NO: 37) | RSDNLSR (SEQ ID NO: 38) | TNQNRIT (SEQ ID NO: 39) |
| 9737 | RQDCLSL (SEQ ID NO: 40) | RNDNRKT (SEQ ID NO: 37) | RSDNLSR (SEQ ID NO: 38) | TNQNRIT (SEQ ID NO: 39) |
| 9846 | HKHVLDN (SEQ ID NO: 41) | RNDNRKT (SEQ ID NO: 37) | RSDNLSR (SEQ ID NO: 38) | TNQNRIT (SEQ ID NO: 39) |
| 8653 | RSANLAR (SEQ ID NO: 42) | RSDNLRE (SEQ ID NO: 43) | QSSNLAR (SEQ ID NO: 44) | QSADRTK (SEQ ID NO: 45) |

Cleavage Domains

Any zinc finger that binds to a target site in a GR gene can be combined with a nuclease to form a zinc finger nuclease. As noted above, any cleavage domain or cleavage half-domain can be used in the zinc finger nucleases described herein. See, U.S. Patent Publication 2005-0064474. Thus, the cleavage domain portion of the fusion proteins disclosed herein can be obtained from any endo- or exonuclease. Exemplary endonucleases from which a cleavage domain can be derived include, but are not limited to, restriction endonucleases and homing endonucleases. See, for example, 2002-2003 Catalogue, New England Biolabs, Beverly, Mass.; and Belfort et al. (1997) Nucleic Acids Res. 25:3379-3388. Additional enzymes which cleave DNA are known (e.g., 51 Nuclease; mung bean nuclease; pancreatic DNase I; micrococcal nuclease; yeast HO endonuclease; see also Linn et al. (eds.) Nucleases, Cold Spring Harbor Laboratory Press, 1993). One or more of these enzymes (or functional fragments thereof) can be used as a source of cleavage domains and cleavage half-domains. In certain embodiments, the cleavage domain is obtained from a nuclease that has separable binding and cleavage domains, for example a yeast HO endonuclease.

Exemplary cleavage half-domains can be obtained from any endonuclease. In certain embodiments, the cleavage half-domain is obtained from a nuclease that has separable binding and cleavage domains, for example a Type IIS restriction endonuclease such as FokI. In addition, engineered cleavage half-domains (also referred to as dimerization domain mutants) that minimize or prevent homodimerization are described, for example, in U.S. Patent Application Publication Nos. 2005-0064474 and 2006-0188987, incorporated by reference in their entireties herein. Amino acid residues at positions 446, 447, 479, 483, 484, 486, 487, 490, 491, 496, 498, 499, 500, 531, 534, 537, and 538 of Fok I are all targets for influencing dimerization of the Fok I cleavage half-domains.

Described herein are additional engineered cleavage half-domains of Fok I that form an obligate heterodimer. The first cleavage half-domain includes mutations at amino acid residues at positions 490 (E in the wild-type sequence, underlined below) and 538 (I in the wild-type sequence, underlined below) of Fok I and the second cleavage half-domain includes mutations at amino acid residues 486 (Q in the wild-type sequence, underlined below) and 499 (I in the wild-type sequence, underlined below).

```
Wild type FokI cleavage half domain
                                          (SEQ ID NO: 46)
QLVKSELEEKKSELRHKLKYVPHEYIELIEIARNSTQDRILEMKVMEFF

MKVYGYRGKHLGGSRKPDGAIYTVGSPIDYGVIVDTKAYSGGYNLPIGQ

ADEMQRYVEENQTRNKHINPNEWWKVYPSSVTEFKFLFVSGHFKGNYKA

QLTRLNHITNCNGAVLSVEELLIGGEMIKAGTLTLEEVRRKFNNGEINF

E490K: I538K dimerization mutant
                                          (SEQ ID NO: 47)
QLVKSELEEKKSELRHKLKYVPHEYIELIEIARNSTQDRILEMKVMEFF

MKVYGYRGKHLGGSRKPDGAIYTVGSPIDYGVIVDTKAYSGGYNLPIGQ

ADEMQRYVKENQTRNKHINPNEWWKVYPSSVTEFKFLFVSGHFKGNYKA

QLTRLNHKTNCNGAVLSVEELLIGGEMIKAGTLTLEEVRRKFNNGEINF

Q486E: I499L dimerization mutant
                                          (SEQ ID NO: 48)
QLVKSELEEKKSELRHKLKYVPHEYIELIEIARNSTQDRILEMKVMEFF

MKVYGYRGKHLGGSRKPDGAIYTVGSPIDYGVIVDTKAYSGGYNLPIGQ

ADEMERYVEENQTRNKHLNPNEWWKVYPSSVTEFKFLFVSGHFKGNYKA

QLTRLNHITNCNGAVLSVEELLIGGEMIKAGTLTLEEVRRKFNNGEINF
```

As shown above, the mutation at 490 replaces Glu (E) with Lys (K); the mutation at 538 replaces Ile (I) with Lys (K); the mutation at 486 replaces Gln (Q) with Glu (E); and the mutation at position 499 replaces Ile (I) with Leu (L). Specifically, the engineered cleavage half-domains described herein were prepared by mutating positions 490 (E→K) and 538 (I→K) in one cleavage half-domain to produce an engineered cleavage half-domain designated "E490K:I538K" as shown above, and by mutating positions 486 (Q→E) and 499 (I→L) in another cleavage half-domain to produce an engineered cleavage half-domain designated "Q486E:I499L" as shown above. These mutations result in a diminished ability of two cleavage half-domains containing the E490K:I538K mutations to form a homodimer, (compared to wild-type FokI cleavage half-domains); similarly, two cleavage half-domains containing the Q486E: I499L mutations are also unable to form a homodimer. However, a cleavage half-domain containing the E490K: I538K mutation is capable of forming a heterodimer with a cleavage half-domain containing the Q486E:I499L mutations to reconstitute a functional cleavage domain capable of double-strand DNA cleavage. Furthermore, heterodimerization between E490K:I538K- and Q486E:I499L-containing cleavage half-domains occurs with an efficiency similar to that of dimerization between wild-type FokI cleavage half-domains. Thus, the engineered cleavage half-domains described herein are obligate heterodimer mutants in which aberrant cleavage is minimized or abolished.

Engineered cleavage half-domains described herein can be prepared using any suitable method, for example, by site-directed mutagenesis of wild-type cleavage half-domains (e.g., Fok I) as described in U.S. Patent Application Publication No. 2005-0064474 (Example 5) and U.S. patent application Ser. No. 11/493,423 (Example 38), incorporated by reference in their entireties herein.

Methods of Treatment

In certain types of cancer immunotherapy, T-cells are engineered to express cell-surface proteins that recognize tumor cell-specific antigens, and these engineered T-cells are introduced into a subject. For example, glioblastoma patients, who have tumor cells that overexpress an IL-13 receptor on their surface, can be treated, following surgical resection of the tumor(s), with cytolytic T-cells that express a "zetakine" tethered to their cell surface. Zetakines are chimeric transmembrane immunoreceptors, comprised of an extracellular domain comprising a soluble receptor ligand linked to a support region capable of tethering the extracellular domain to a cell surface, a transmembrane region and an intracellular signaling domain. When expressed on the surface of T lymphocytes, such chimeric receptors direct T cell activity to those specific cells expressing a receptor for which the soluble receptor ligand is specific.

For treatment of gliomas and glioblastomas, zetakines are targeted to cells expressing IL-13 receptors. Thus, a zetakine can constitute a glioma-specific immunoreceptor comprising the extracellular targeting domain of the IL-13Ralpha.2-specific IL-13 mutant IL-13(E13Y) linked to the Fc region of IgG, the transmembrane domain of human CD4, and the human CD3 zeta chain. T-cells expressing such a zetakine are able to detect and kill IL-13-overexpressing glioma and glioblastoma tumor cells remaining after surgical tumor resection. See, for example, Kahlon, K. S. et al. (2004) Cancer Res. 64:9160-9166 and US patent application publication numbers 2006-0067920, 2005-0129671, and 2003-0171546, the disclosures of which are incorporated by reference in their entireties for all purposes.

However, the clinical use of this approach is hampered by the fact that brain tumor patients must also be treated with glucocorticoid hormones following tumor resection, to prevent inflammation and swelling of the brain. This glucocorticoid treatment inhibits activation of the zetakine-containing T-cells, thus preventing their cell-killing activity.

The methods and compositions disclosed herein make it possible to eradicate GR function in the zetakine-containing T-cells, thereby making them resistant to the inhibitory effect of glucocorticoids. Accordingly, by use of the disclosed methods and compositions, the post-surgical glioblastoma patient can be treated both with glucocorticoids (to prevent swelling and inflammation) and with the zetakine-containing T-cells, to remove residual tumor cells. Indeed, inactivation of the GR gene in the T-cells can be accomplished by targeted integration of a sequence encoding the zetakine into the GR locus, accomplishing both objectives in a single step.

Accordingly, in certain embodiments, GR-targeted zinc finger nucleases are expressed in T-cells and cleave at a site in the GR locus. Cells containing GR-targeted zinc finger nucleases are optionally contacted with a donor DNA molecule which encodes a zetakine, such that the zetakine-encoding sequences are integrated into the GR locus, thereby inactivating GR function in those cells.

Additional Applications

Treatment of patients with engineered T-cells or isolated T-cells is compromised if these patients are also treated with immune-suppressant drugs such as decadrone. However, modification of such therapeutic immune cells, using ZFNs targeting the GR locus to inactivate GR function as disclosed herein, allows generation of a population of immune cells that is not subject to glucocorticoid-mediated immune suppression. The high efficiency of the methods described herein allows simultaneous disruption of both alleles of the GR gene in the absence of a selection marker, which is not possible with any other technique. The speed with which mutations in both alleles of the GR gene (including homozygous deletions) can be obtained is also an important consideration since T-cells, like all primary cells, have a limited replication potential and therefore a finite lifespan.

The methods disclosed herein for modification of the sequence of the GR locus in human cells allow generation of pools of cells containing a substantial number of cells lacking GR function and also allow isolation of clonal cell lines lacking GR activity. Such cells include but are not limited to T-cells and other cells of the immune system (e.g., B-cells, NK cells, memory cells, macrophages) all of which are normally prevented from undergoing proper activation in the presence of glucocorticoid hormones, due to the action of the glucocorticoid receptor.

As discussed above, one application of these methods is the use of ZFNs to render zetakine expressing T-cells, which target brain tumor cells, non-responsive to glucocorticoids. Other examples include ZFN-mediated inactivation of GR in T-cells used for treating opportunistic infections, e.g., in transplant patients receiving immunosuppressants, or in other immunocompromised patients.

Additional clinical complications of undesired GR activity can also be alleviated by inactivation of GR activity in a specific target cell population. In this context, it is noted that the pleiotropic activity of the GR is based, in part, on the existence of multiple receptor isoforms generated from the same gene. See, for example, Zhou, J. et al. (2005) *Steroids* 70:407-417. The single nucleotide-level resolution of ZFN-mediated GR gene modifications described herein, in combination with tissue-specific ZFN expression, (see, for example, U.S. Pat. No. 6,534,261 and U.S. Patent Application Publication No. 2005-0064474, both incorporated by reference) together enable disruption of specific receptor isoforms in specific tissues: an approach that is not possible with any other technology. In addition, alteration of the sequence of the GR gene using ZFNs can be used to replace the wild-type GR with an isoform that is regulated exclusively by a specific ligand of choice.

Conversely, in patients with mutations in the GR locus, ZFN-mediated genome editing can be used to restore GR activity in a target tissue of choice, either through correction of the mutation itself or by targeted insertion of a sequence (e.g., cDNA) encoding a functional GR.

The methods and compositions disclosed herein can also be used to generate cell lines for research applications, drug screening and target validation. For instance, abolishing GR function in a cell line of choice, using ZFNs as disclosed herein, allows generation of a matched pair of isogenic cell lines that differ only in the presence or absence of GR function. As another example, insertion of a reporter gene into the GR locus, or fusion of a reporter to the GR protein, will facilitate high-resolution studies of the properties and regulation of the glucocorticoid receptor. Such lines can be used for research purposes, as well as for industrial applications such as target validation and drug screening. Similarly, ZFN-mediated gene correction can be used to introduce specific changes into the GR locus to generate cell lines for studying the function of various receptor domains or isoforms.

Finally, in cases in which inactivation of the GR locus is not the main purpose of the intervention, but would have no negative effects on the modified cells, the GR locus can be used as a "safe harbor" integration site for any transgene in any gene therapy application. Thus, the disclosure also provides methods of selection for cells into which an exogenous sequence has been integrated into a GR gene. The methods involve cleaving an endogenous GR gene in a cell with ZFNs as described herein and introducing an exogenous sequence (e.g., transgene), typically on a donor construct with GR-homology arms, into the cells under conditions such that the exogenous sequence is integrated into the GR gene. Cells with the integrated exogenous sequence can then be selected for by exposing the cells to a naturally occurring or synthetic corticosteriod (e.g., cortisol, dexamethasone, etc.), which kills cells without the integrated sequence (cells with normal GR expression). See, also, Example 4.

Vectors for Delivery of Zinc Finger Nucleases and Donor DNA Sequences

Any vector can be used for delivery, to a cell, of DNA sequences encoding zinc finger nucleases and/or delivery of donor DNA. Exemplary viral vectors include adenoviruses, adeno-associated viruses, poxviruses, herpesviruses, papovaviruses, retroviruses and lentiviruses. DNA can also be delivered to cells by transfection, electroporation, lipid-mediated methods, biolistics and calcium phosphate-mediated transfer.

Because the methods and compositions disclosed herein utilize a transient event (ZFN-mediated double-strand cleavage) to effect a permanent genomic alteration (e.g., targeted mutation or targeted integration of exogenous sequences), it is not necessary to use a delivery vector that persists in the cells. Accordingly, non-replicating viral vectors can be used as delivery vehicles. Thus, replication-defective adenoviruses, hybrid adenoviruses (e.g., Ad 5/35) and non-integrating lentivirus vectors are all suitable as delivery vehicles.

Non-limiting examples of adenovirus (Ad) vectors that can be used in the present application include recombinant (such as E1 deleted), conditionally replication competent (such as oncolytic) and/or replication competent Ad vectors derived from human or non-human serotypes (e.g., Ad5, Ad11, Ad35, or porcine adenovirus-3); chimeric Ad vectors (such as Ad5/35) or tropism-altered Ad vectors with engineered fiber knob proteins (such as peptide insertions within the HI loop of the knob protein); and/or "gutless" Ad vectors, e.g., an Ad vector in which all adenovirus genes from the Ad genome have been removed to reduce immunogenicity and to increase the size of the DNA payload to allow simultaneous delivery of both ZFNs and donor molecule, especially large transgenes to be integrated via targeted integration.

Replication-deficient recombinant adenoviral vectors (Ad) can be produced at high titer and readily infect a number of different cell types. Most adenovirus vectors are engineered such that a transgene replaces the Ad E1a, E1b, and/or E3 genes; subsequently the replication defective vector is propagated in human 293 cells that supply deleted gene function in trans. Ad vectors can transduce multiple types of tissues in vivo, including nondividing, differentiated cells such as those found in liver, kidney and muscle. Conventional Ad vectors have a large carrying capacity. An example of the use of an Ad vector in a clinical trial involved polynucleotide therapy for antitumor immunization with intramuscular injection. Sterman et al. (1998) *Hum. Gene Ther.* 7:1083-1089.

Additional examples of the use of adenovirus vectors for gene transfer in clinical trials include Welsh et al. (1995) *Hum. Gene Ther.* 2:205-218; Rosenecker et al. (1996) *Infection* 24:5-10; Alvarez et al. (1997) *Hum. Gene Ther.* 5:597-613 and Topf et al. (1998) *Gene Ther.* 5:507-513.

In certain embodiments, the Ad vector is chimeric adenovirus vector, containing sequences from two or more different adenovirus genomes. For example, the Ad vector can be an Ad5/35 vector. Ad5/35 is created by replacing the fiber protein of Ad5 with the fiber protein from B group Ad35. The Ad5/35 vector and characteristics of this vector are described, for example, in Ni et al. (2005) *Hum. Gene Ther.* 16:664-677; Nilsson et al. (2004) *Mol. Ther.* 9:377-388; Nilsson et al. (2004) *J. Gene. Med.* 6: 631-641; Schroers et al. (2004) *Exp. Hematol.* 32:536-546; Seshidhar et al. (2003) *Virology* 311:384-393; Shayakhmetov et al. (2000) *J. Virol.* 74:2567-2583 and Soya et al. (2004) *Mol. Ther.* 9:496-509.

EXAMPLES

The following examples are presented as illustrative of, but not limiting, the claimed subject matter.

Example 1

Construction of Plasmid Delivery Vehicles Encoding Zinc Finger Nucleases Targeted to a Human GR Gene Target sites for zinc finger DNA-binding domains were selected by scanning the sequence of the human glucocorticoid receptor (GR) gene, optionally using a computer program containing a listing of individual zinc fingers and their target sites and/or a listing of two-finger modules and their target sites, for a pair of target sequences, separated by 5-6 nucleotide pairs, wherein each target sequence can be bound by a 3-, 4-, 5- or 6-finger zinc finger protein. See, for example, U.S. Pat. No. 6,785,613; WO 98/53057; WO 01/53480 and U.S. Patent Application Publication No. 2003/0092000. Additional methods for ZFP design are disclosed, for example, in U.S. Pat. Nos. 5,789,538; 6,013,453; 6,410,248; 6,733,970; 6,746,838; 6,785,613; 6,866,997; 7,030,215; WO 01/088197; WO 02/099084; and US Patent Application Publications 2003/0044957; 2003/0108880; 2003/0134318 and 2004/0128717.

For certain of the target sequences identified in the previous step, a gene encoding a fusion between a FokI cleavage half-domain and a zinc finger protein that binds to the target sequence was synthesized. See, for example, U.S. Pat. No. 5,436,150; WO 2005/084190 and U.S. Patent Application Publication No. 2005/0064474.

Figure 1:
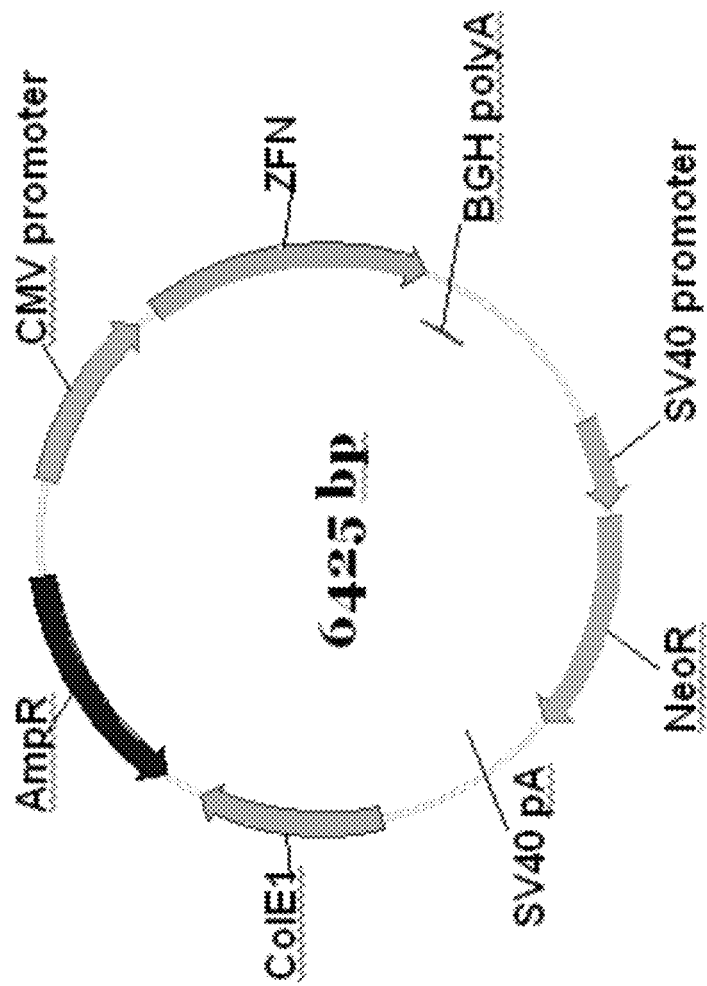
FIG. 1 is a schematic diagram of an exemplary plasmid construct encoding a zinc finger nuclease. "CMV promoter" denotes the human cytomegalovirus immediate early promoter, "ZFN" denotes sequences encoding a zinc finger nuclease (e.g., a zinc finger DNA-binding domain fused to a cleavage half-domain), "BGH polyA" denotes the polyadenylation signal from the bovine growth hormone gene, "SV40 promoter" denotes the major promoter from simian virus 40, "NeoR" denotes an open reading frame encoding neomycin resistance, "SV40 pA" denotes the polyadenlyation signal from the simian virus 40 major transcription unit, "ColE1" denotes a replication origin from Colicin E1 and "AmpR" denotes the β-lactamase gene encoding ampicillin resistance.
Figure 2:
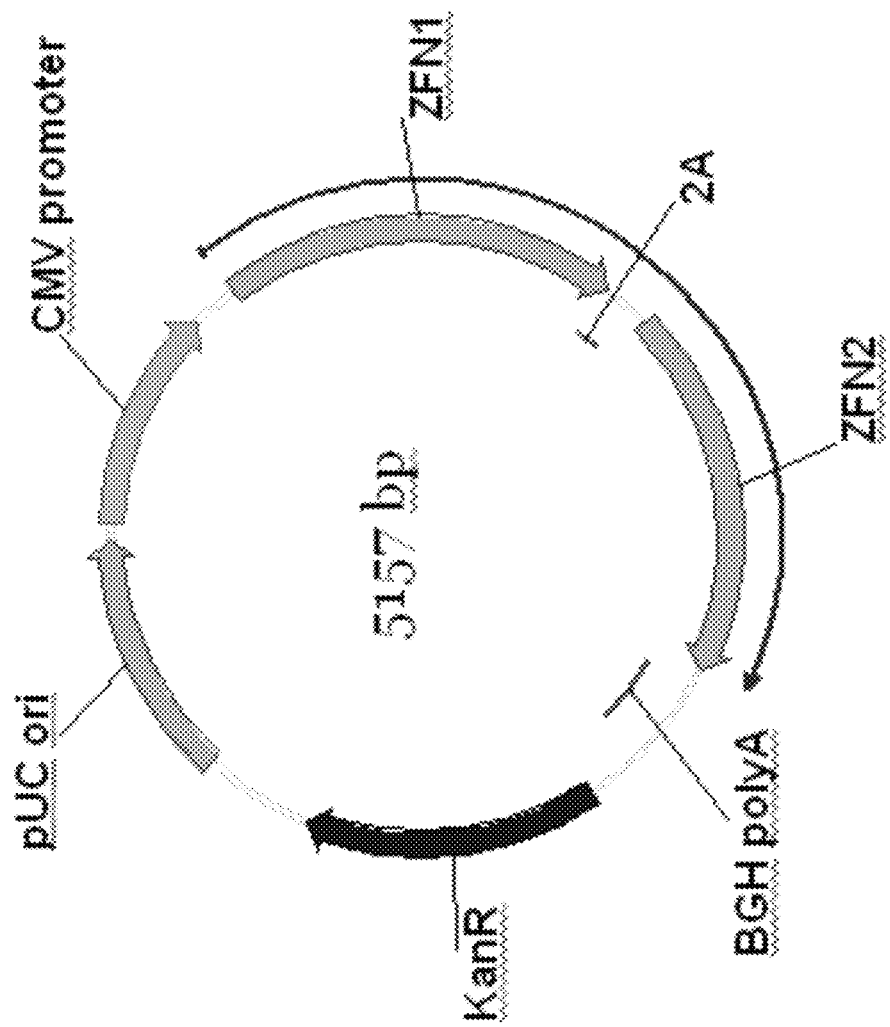
FIG. 2 is a schematic of an exemplary plasmid construct encoding two different zinc finger nucleases. Abbreviations are the same as in FIG. 1 with the following additions. "2A" denotes the Foot-and-Mouth Disease virus (FMDV) ribosome stuttering signal, "KanR" denotes an open reading frame which encodes kanamycin resistance and "pUC ori" denotes the origin of replication from the pUC 19 plasmid.

Standard molecular biological methods were used to construct such fusion genes and introduce them into plasmids. Exemplary expression constructs are shown in FIGS. 1 and 2.

Example 2

Targeted Cleavage of a Human GR Gene Using Engineered Zinc Finger Nucleases

K562 cells (ATCC No. CCL243) were cultured in RPMI medium (Invitrogen, Carlsbad, Calif.). At a density of $1 \times 10^6$ cells/ml, $2 \times 10^6$ cells were pelleted and transfected with 2.5 µg each of two ZFN expression vectors, using an Amaxa nucleofection device (Amaxa, Gaithersburg, Md.). One set of cells was transfected with plasmids encoding zinc finger nucleases comprising the exon 3-targeted 9666 and 9674 binding domains (see Tables 1 and 2). A second set of cells was transfected with plasmids encoding zinc finger nucleases comprising the exon 6-targeted 8653 and 9737 binding domains (see Tables 1 and 2). Controls included cells transfected with a plasmid encoding green fluorescent protein (GFP) and untransfected cells.

Three days after transfection, DNA was isolated from the cells using a DNeasy® kit (Qiagen, Valencia, Calif.). This DNA (100 ng) was used as template for PCR amplification using primers specific for either exon 3 or exon 6 of the GR locus (see Table 3). The amplification products were denatured, then reannealed; and the reannealed products were exposed to the mismatch-specific nuclease Cel-I (Transgenomic, Omaha, Nebr.). Products of Cel-I treatment were analyzed on a 10% polyacrylamide gel. If the population of amplification products is homogeneous with respect to nucleotide sequence, perfectly-matched duplexes, that are resistant to Cel-I cleavage, should be produced following denaturation and reannealing. If, on the other hand, the amplification products are heterogeneous due to the presence of insertions, deletions and/or mismatches in some of the amplification products, reannealing will generate some duplexes containing sequence mismatches, susceptible to Cel-1 cleavage. As a result, products smaller than the amplification product will be detected on the gel.

TABLE 3

| PCR primers in the human GR locus | | |
|---|---|---|
| Exon 3 sense | TCATAACACTGTTCTTCCCCTTCTTTAGCC | (SEQ ID NO: 49) |
| Exon 3 antisense | TCAAAACACACACTACCTTCCACTGCTC | (SEQ ID NO: 50) |
| Exon 6 sense | ACACCTGGATGACCAAATGACCCTAC | (SEQ ID NO: 51) |
| Exon 6 antisense | CCTAGATACCTAGTAGGATTGTTTCAGTCCTG | (SEQ ID NO: 52) |

Figure 3A:
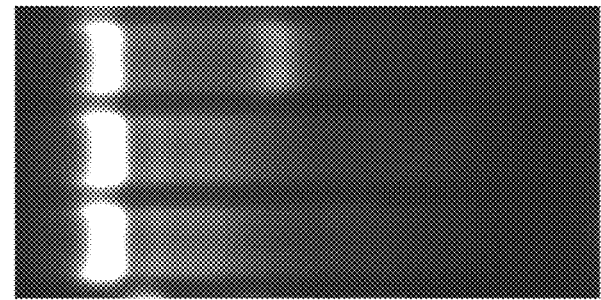
FIGS. 3A and 3B, show the results of Cell assays demonstrating cleavage by ZFNs in the GR locus in hematopoietic cells (K562).
Figure 3B:
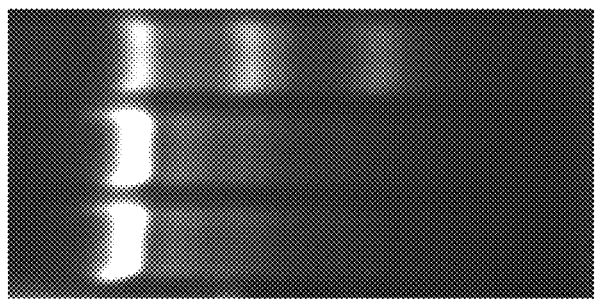

The results are shown in FIG. 3. Amplification products of exon 3- and exon 6-specific DNA from untransfected cells, and from cells transfected with a plasmid encoding GFP, yield a single band after denaturation, reannealing and Cel I treatment (left and middle lanes, respectively, of each panel), indicative of a homogeneous population of amplification products. By contrast, exon 3-specific amplification products from cells transfected with plasmids encoding zinc finger nucleases having zinc finger DNA-binding domains with target sites in exon 3 (9666 and 9674) yield two smaller products after denaturation, reannealing and Cel I treatment (left panel, rightmost lane). The presence of these smaller products indicates the existence of a sequence mismatch at a unique location in the reannealed DNA. Similarly, exon 6-specific amplification products from cells transfected with plasmids encoding zinc finger nucleases having zinc finger DNA-binding domains with target sites in exon 6 (8653 and 9737) yield two smaller products (of similar molecular weight), indicative of targeted cleavage in exon 6.

Example 3

Nature of Mutations Induced by Targeted Cleavage in a Human GR Gene

CEM14 cells (a glucocorticoid-sensitive lymphoid cell line obtained from M. Jensen, City of Hope Medical Center, Duarte, Calif.) were cultured in RPMI medium. At a density of $1 \times 10^6$ cells/ml, $2 \times 10^6$ cells were pelleted and transfected with plasmids encoding ZFNs with the exon 3-targeted 8667 and 8668 DNA-binding domains (see Tables 1 and 2), using an Amaxa nucleofection device. 2.5 µg of each plasmid was used. Cells lacking GR function were selected by exposure to $10^{-5}$ M dexamethasone for 14 days; and DNA isolated from dexamethasone-resistant cells was amplified by PCR using GR exon 3-specific primers (see Table 3). The amplification reaction mixture was fractionated on an agarose gel and a band corresponding in size to the expected amplification product (based on the location of the primer sequences in the GR gene) was excised from the gel. DNA in this band was cloned using a Topo® cloning kit (Invitrogen, Carlsbad, Calif.) and nucleotide sequences of individual clones was determined.

In one clone, sequence analysis revealed the presence of a two-nucleotide deletion near the site of targeted cleavage. In a second clone, an 11-nucleotide deletion was detected. A third clone comprised a mixture of sequences: one of which was a duplication of four nucleotides, the other of which was a 19-nucleotide deletion.

These results show that targeted cleavage of the GR gene, using zinc finger nucleases, induced both insertion and deletion mutations in the gene, all of which resulted in a change in the translational reading frame.

RNA analysis in these dexamethasone-resistant cells revealed lower levels of GR mRNA, compared to untransfected cells; indicative of nonsense-mediated decay of aberrant GR transcripts.

Example 4

Introduction of a Transgene into the Human GR Locus

Glucocorticoid hormones trigger apoptosis or slow down cell growth in many primary cells and cell lines. Glucocorticoid hormone treatment can therefore be used in combination with ZFNs targeting the GR locus to select or enrich for a) cells containing a ZFN mediated biallelic mutation of the GR locus, b) cells containing ZFN mediated targeted integration of donor DNA sequences into both alleles of the GR locus, resulting in the inactivation of GR function or c) cells containing a ZFN mediated GR mutation on one allele of the GR locus and ZFN mediated targeted integration on the other allele.

Sequences that can be integrated into the GR locus in this manner include but are not limited to expression cassettes with any transgene of choice. Potential benefits of using integration into the GR locus include but are not limited to a) avoiding the use of a selection marker on the donor molecule, b) long term stability of the expression of the transgene from a locus compatible with high level gene expression and not subjected to silencing, c) avoiding insertional mutagenesis events that can occur upon random integration of transgenes. The following experiments were conducted using a zetakine transgene.

Figure 4B:
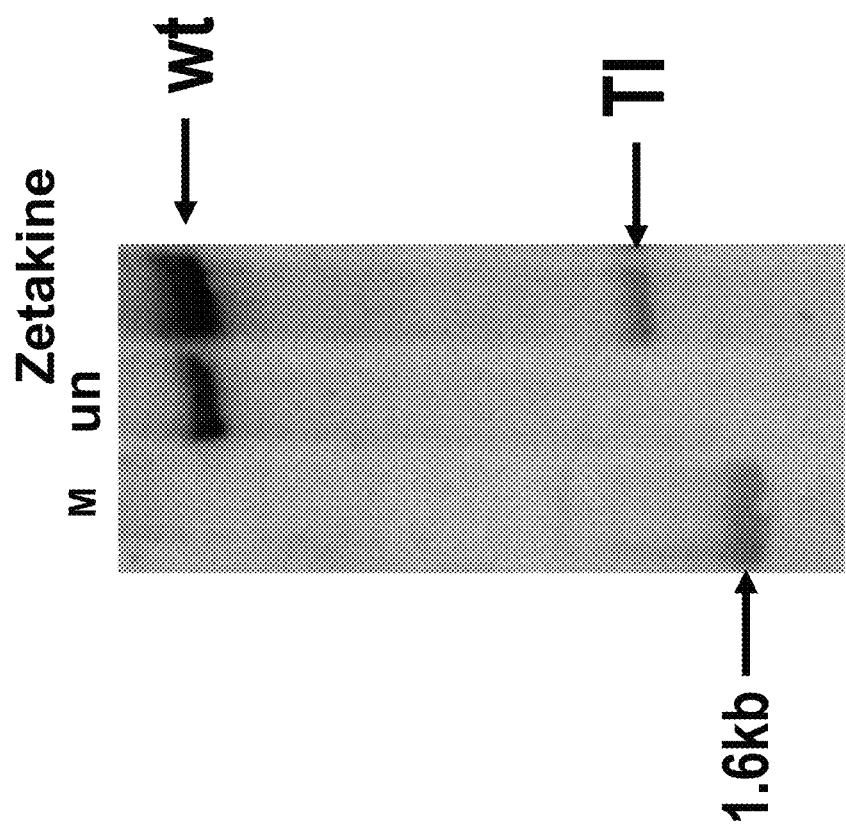
FIGS. 4A and 4B, show ZFN mediated targeted integration of a zetakine transgene into the GR locus.
Figure 4A:
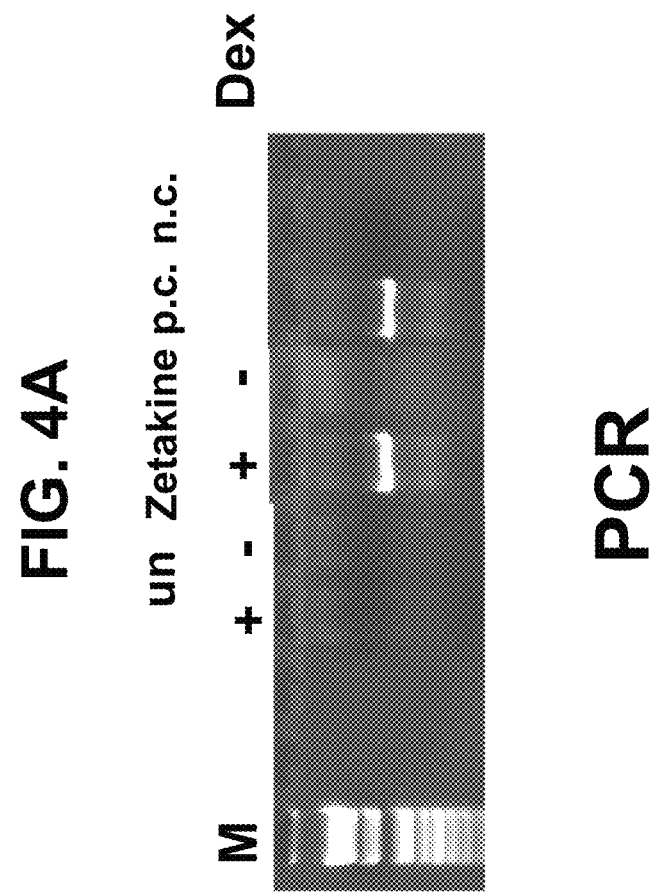

CEM14 cells were cultured in RPMI medium and transfected (as described in previous examples), in separate experiments, with 25 µg of an expression construct encoding the GR-targeted ZFNs 9666 and 9674 and a zetakine transgene. The zetakine-donor ZFN construct was transfected into CEM14 cells and an aliquot of the transfected cells was incubated with dexamethasone (which kills cells having normal GR function) for 2 weeks, while the remaining cells were left untreated. Untransfected cells were used as controls and treated identically. After dexamethasone treatment, targeted integration of the zetakine transgene into the GR locus was detected by PCR (FIG. 4A) and by Southern blotting (FIG. 4B). Immunostaining shows high-level zetakine expression in the dexamethsone selected CEM14 cells transfected with both the GR ZFNs and the zetakine donor construct (not shown).

These results demonstrated that targeted integration of a donor sequence in the human GR gene was accomplished, that integration of the donor sequence inactivated GR function, and that normal function of a transgene contained in the donor sequence was obtained.

Example 5

GR Polypeptide Production after Targeted Integration of an Exogenous Sequence in the GR Gene CEM14 cells were cultured in RPMI medium and transfected as above with 25 µg of an expression vector containing a zetakine cassette and encoding the GR exon 3-targeted ZFN pair 8667 and 8669, flanked by regions of homology to the GR gene. Two days after transfection, $10^{-6}$ M dexamethasone was added to the growth medium, and glucocorticoid-resistant clones were obtained after two weeks of selection.

Protein extracts from transfected cells that survived the dexamethasone treatment were prepared by whole cell lysis, and Western Blot analysis was performed using an antibody to the human GR (Catalog number 611226, BD BioSciences Pharmingen, San Jose Calif.). Results are shown in FIG. 5. A band corresponding to the wild-type receptor was detected in untransfected CEM 14 cells (left lane), while a clone of CEM14 cells treated with the ZFNs and the donor sequence contained no immunoreactive material corresponding to the size of the wild-type receptor; instead, a band corresponding in size to a truncated receptor form was detected (right lane).

Example 6

Targeted Cleavage of a Human GR Gene in CD8+ T-Cells

Fresh human peripheral blood CD8+ T-Cells were obtained from AllCells (Berkeley, Calif.). $2 \times 10^6$ cells were transfected, using an Amaxa nucleofection device and protocol, with 5 µg of an expression plasmid encoding two zinc finger nucleases targeting exon 3 of the human GR locus, in which the ZFN coding sequences were separated by a 2A sequence. Two exon 3-targeted ZFN pairs (9666-9671 and 9666-9674) were tested in separate transfections. Controls were untransfected cells and cells transfected with a plasmid encoding green fluorescent protein (GFP).

Transfected CD8+ cells were cultured for 48 hours in X-VIVO15 medium containing 5% human serum (both purchased from Cambrex, Walkersville, Md.). Thereafter, DNA was isolated and Cel I analysis was performed as described in Example 2 above, using exon 3-specific amplification primers, except that 5 µCi each of α-$^{32}$P-dCTP and α-$^{32}$P-dATP (Perkin-Elmer, Boston, Mass.) were added to the PCR reaction.

Figure 6:
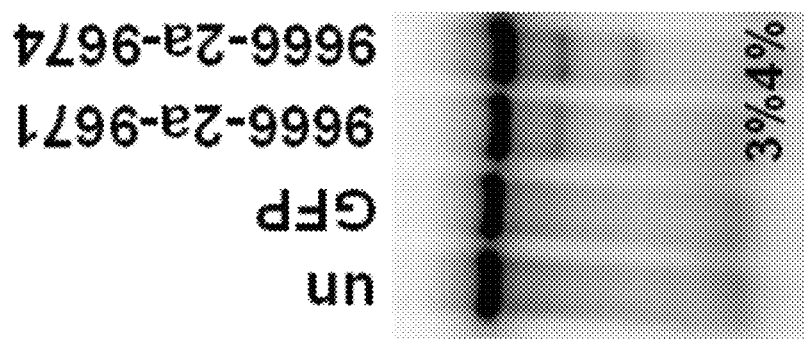
FIG. 6 shows the results of Cel I assays demonstrating cleavage by ZFNs in exon 3 of the GR locus in CD-8$^+$ T-cells. An autoradiogram of a 10% acrylamide gel is shown. Abbreviations are as follows: "un" denotes untransfected cells, "GFP" denotes cells transfected with a plasmid encoding green fluorescent protein. The identities of the zinc finger portion of the zinc finger nucleases expressed in the transfected cells are shown above the two rightmost lanes; see Tables 1 and 2 for details.

Following Cel I treatment, digestion products were fractionated on a 10% acrylamide gel. An autoradiographic image of the gel was developed using a Storm Phosphorlmager (GE Healthcare, Piscataway, N.J.). Results are shown in FIG. 6. Frequencies of non-homologous end joining (NHEJ) were determined by quantitation of the Cel I cleavage products and are indicated in the rightmost two lanes of FIG. 6. Thus, GR-targeted ZFNs efficiently modify the GR locus in the CD8+ T-cells.

Example 7

Analysis of GR-ZFN-Treated CD-8$^+$ T-Cells

A. ZFNs Generate Mutations at GR Locus

Fifty million human CD8+ T-cells cells expressing a zetakine transgene ('IL-13 ZK Pool') were stimulated at day 0 and infected at day 7 with Ad5/F35 expressing the ZFN pair 9666 and 9674 at the following multiplicity of infections (mois): 10 ("ZFN10-"), 30 ("ZFN30-") and 100 ("ZFN100-"). As a control, CD8+ cells were also infected with a GFP expressing Ad5/F35 virus at the same mois ("GFP10-", "GFP30-", "GFP100-").

Cells were grown as described above and 7 days postinfection cells were treated for 6 days with the glucocorticoid hormone dexamethasone at a concentration of 10$^{-4}$ M in the absence of cytokines. The resulting cell pools ('ZFN10', 'ZFN30', 'ZFN100' and 'GFP10', 'GFP30', 'GFP100', respectively) were restimulated and 12 days after restimulation cells were harvested. DNA was isolated and analyzed for modification of the GR locus by PCR of the ZFN target region followed by the Cel I Surveyor™ endonuclease assay as described in Example 2 above. As shown in FIG. 7, panels A and B, transient ZFN expression generated GC-Resistant CD8+ T-cells with mutations at the GR locus.

The PCR products were also subcloned into the PCR4 TOPO vector and the insert sequence analyzed using the T7 primer. Sequencing of the ZFN target region in exon 3 of the GR locus in cells pool ZFN100 demonstrated that 70% of the GR alleles contained mutations in the ZFN binding region. By contrast, no mutations were found in the GR alleles when cells had been infected with the GFP100 control virus.

Glucocorticoid hormone resistance of the CD8+ cell pools was also determined by comparing cell viability before and after a second treatment with 10-4M Dexamethasone for 8 days. Viability was measured using the Guava cell analyzer. As shown in FIG. 8, ZFN treated cells showed increased resistance to glucocorticoid hormone.

B. GR Protein Expression in ZFN-Modified CD8+ T-Cells

ZFN-treated CD8+ T-cells were also tested for the presence of full-length GR protein.

Figure 9A:
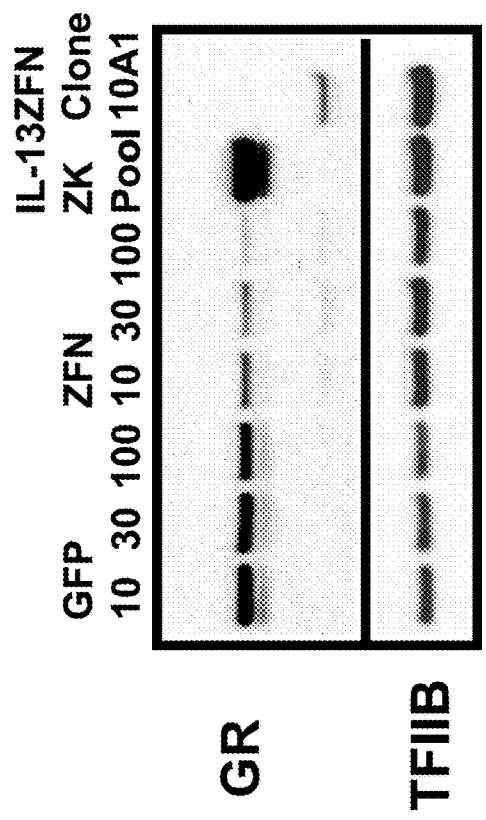
FIGS. 9A and 9B, show Western blot analysis for GR protein from two separate experiments. Panel A shows results of proteins extracted from CD8+ cell pools described in Example 7; from the zetakine expressing CD8+ cell pool that was used for the virus transduction ('IL-13 ZK pool'); and from a subclone ('10A1') of the ZFN 100 pool. The antibody used for probing each panel is listed to the left of the blot. TFIIB (Santa Cruz Antibodies) was used as a loading control. The GR antibody was obtained from BD Biosciences. Panel B shows GR protein levels in various subclones of CD8+ cells with specificity to CMV treated with the GR-ZFN expressing Ad5/F35 virus. Clone names are indicated above the lanes and "mock" refers to the mock infected starting CMV-targeted CD8+ cell pool.

In one experiment, protein extract from CD8+ cell pools described above and from the zetakine expressing CD8+ cell pool that was used for the virus transduction ('IL-13 ZK pool') were analyzed by Western Blotting using GR (BD BioSciences) and TFIIB (Santa Cruz Antibodies) antibodies. In addition a subclone ('10A1') of the ZFN 100 pool was analyzed alongside the cell pools. As shown in FIG. 9A, ZFN treated CD8+ T-cells showed a loss of GR protein as compared to controls.

Figure 9B:
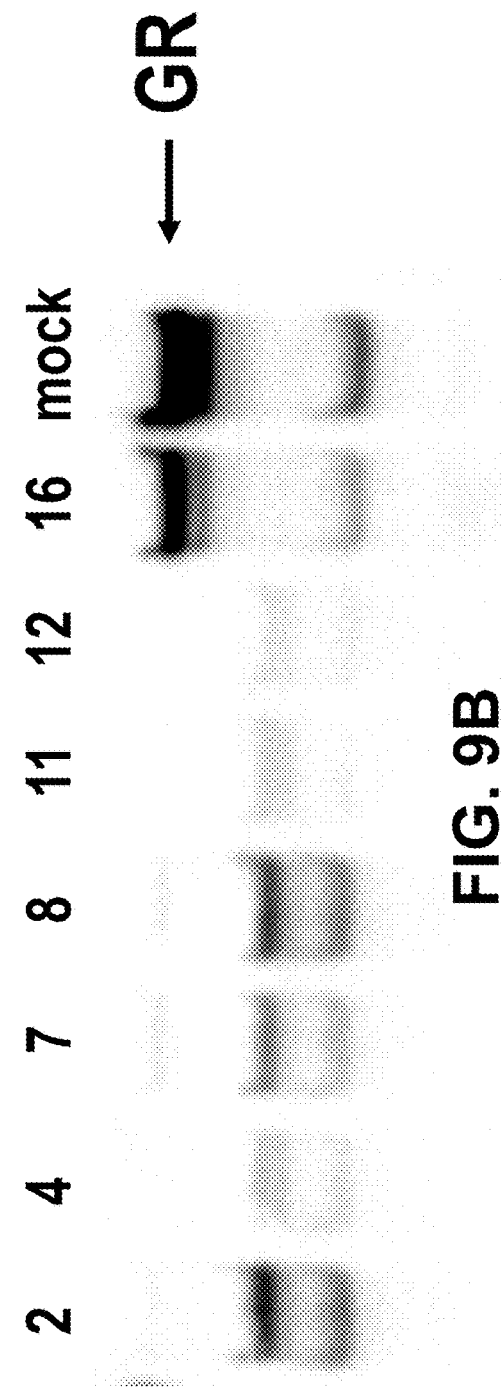

In a separate experiment, expression of GR was also assessed in ZFN treated CMV-targeted CD8+ subclones. In particular, GR-negative CD8+ cells that target CMV were generated using ZFNs as described herein. Single cell derived subclones of these cells were isolated and protein extracts were obtained from these clones as described above. Genotyping of 26 subclones identified 2 wildtype clones and 24 clones with mutations in the GR locus comprising the ZFN binding regions. As above, protein extracts were analyzed by Western Blotting with a human GR antibody (BD BioSciences). As shown in FIG. 9B, ZFN-treated CMV-targeted CD8+ clones showed loss of GR protein.

Thus, ZFNs as described herein can reduce or eliminate GR protein expression in primary cells.

C. RT-PCR

In addition, GR-negative (ZFN-treated) CD8+ T-cells were analyzed by RT-PCR to determine the effect of glucocorticoid addition on the expression of known GR target genes. Results are shown in FIGS. 10A-10D. Cells were left untreated ("un") or treated with 10$^{-6}$M dexamethasone for 20 hrs ("dex") as indicated. RNA was isolated using standard protocols, and the mRNA levels of various glucocorticoid regulated genes analyzed by RT-PCR using the Taqman™ protocol (Applied Biosystems). RNA values for GR target genes were corrected by the values for the GAPDH housekeeping gene obtained from the same RNA sample. Taqman probes and primers for GR target genes were obtained from Applied Biosystems. As shown in FIGS. 10A-D, glucocorticoid hormone treatment affected the target genes less in ZFN-treated CD8+ T-cells.

D. Cytokine Release

Cytokine release from ZFN-treated CD8+ T-Cells stimulated with glioma cells was also evaluated. GFP100, ZFN100 and untreated CD8+ T-cell pools were cultured alone or in the presence of U87MG glioblastoma stimulator cells. Subsequently, 10$^{-6}$M dexamethasone was added to the culture. After 20 hrs, cell culture supernatants were harvested and IFN-γ levels analyzed using a commercially available ELISA kit (R&D systems).

Figure 11:
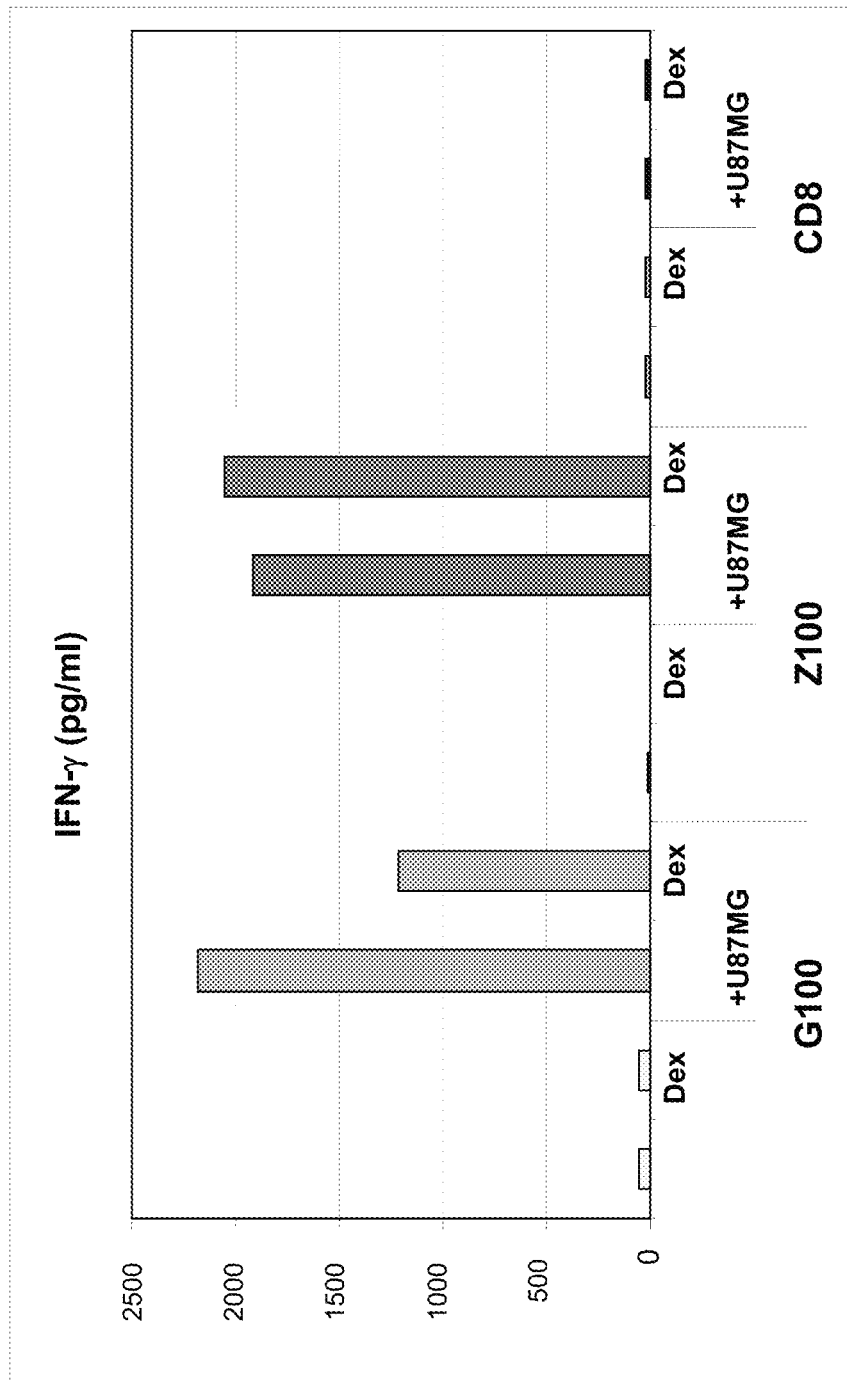
FIG. 11 is a graph depicting IFN-γ cytokine release by ZFN Treated CD8+ T-Cells upon stimulation with glioma cells. The CD8+ T-cell pools are indicated below the bars.

As shown in FIG. 11, cytokine release by ZFN treated CD8+ T-cells upon stimulation with glioma cells was maintained and was rendered resistant to glucocorticoid hormones.

E. Chromium Release Assay for Cytolytic Activity

To analyze the cytolytic activity of ZFN treated CD8+ T-cells chromium release assays were conducted at various ratios of effector (ZFN-treated or control CD8+ T-cells) to target cells (IL13Rα2 positive cell lines and control cell line).

As shown in FIG. 12, panels A to E, ZFN-treated CD8+ T-cells maintain the ability to kill IL13Rα2+ target cells.

Example 8

In Vivo Administration of ZFN-Treated, GR-Negative CD8+ T-Cells

ZFN-treated GR-negative CD8+ T-cells were also analyzed for tumor cell killing activity in vivo. Tumor cell cyotoxicity was measured in an orthotopic glioblastoma mouse model using luciferase labeled U87MG cells injected into the brain at day 0. At day 5, controls or ZFN-treated CD8+ T-cells were injected into the brain and tumor volumes were determined by measuring luciferase activity up to day 24.

As shown in FIG. 13, ZFN-treated GR-negative CD8+ T-cells (panel C) reduced tumor volumes as compared to controls. Furthermore, the experiment shown in FIG. 14 demonstrates that the anti-tumor activity of the ZFN treated GR-negative CD8+ T-cells in the mouse tumor model was not negatively affected by the administration of glucocorticoid hormone. Accordingly, ZFN-treated GR-negative CD8+ T-cells can be administered for treatment of glioblastoma in patients receiving glucocorticoid hormones.

Example 9

Analysis of GR ZFN Specificity

To analyze the specificity of the GR ZFNs 9666 and 9674 in cells, we first determined consensus DNA binding site for both the 9666 and the 9674 ZFNs in vitro using an affinity-based target site selection procedure (SELEX). See, also, U.S. Ser. No. 11/805,707, filed May 23, 2007. An experimental overview is provided in FIG. 15. Briefly, hemaglutinin-tagged ZFNs were incubated with a pool of randomized DNA sequences in the presence of biotinylated anti-HA Fab antibody fragments. The tagged ZFN-DNA complexes were captured with streptavidin-coated magnetic beads, and the bound DNA was released and amplified by PCR. This process was repeated three times using the previous eluted, amplified pool of DNA as a starting sequence. After four iterations, the eluted DNA fragments were sequenced, and base frequencies at each position in the binding sites of ZFN 9666 and ZFN 9674 were determined.

A consensus based on the site selection data was used to guide a genome-wide bioinformatic prediction of the most similar putative off-target sites in the human genome. The resulting list of potential cleavage sites was then ranked to give priority to those sites with the highest similarity to the experimentally derived binding site preferences.

NR3C1 (the GR locus) contains the best match to the binding site preferences determined in the site selection experiments. Of the 15 potential off-target sites, 10 fall within annotated genes, and only 2 occur within exonic sequences. For none of these ten genes, has mutation or disruption been associated with any known pathology in CD8+ T cells.

Genotyping of clone 10A1 (a T cell derived clone) confirmed that none of the 15 sites with highest similarity to the consensus were modified under conditions that resulted in bi-allelic modification of the GR (on-target) locus.

All patents, patent applications and publications mentioned herein are hereby incorporated by reference in their entirety.

Although disclosure has been provided in some detail by way of illustration and example for the purposes of clarity of understanding, it will be apparent to those skilled in the art that various changes and modifications can be practiced without departing from the spirit or scope of the disclosure. Accordingly, the foregoing descriptions and examples should not be construed as limiting.

What is claimed is:

1. An isolated human cell with an inactivated human glucocorticoid receptor (GR) gene, the isolated human cell comprising:
   (i) a first zinc finger nuclease (ZFN) comprising a zinc finger DNA-binding domain comprising the following recognition helices in the following order:
   TSRALTA (SEQ ID NO: 23);
   DRANLSR (SEQ ID NO: 17);
   RSDNLSE (SEQ ID NO: 24);
   ERANRNS (SEQ ID NO:26); and
   (ii) a second zinc finger nuclease (ZFN) comprising a zinc finger DNA-binding domain comprising the following recognition helices in the following order:
   DSWNLQV (SEQ ID NO:33);
   RSANLTR (SEQ ID NO: 27);
   TSGNLTR (SEQ ID NO:30);
   TSGSLTR (SEQ ID NO:31).

2. The isolated human cell of claim 1 comprising one or more polynucleotides encoding the first and second ZFNs.

3. The isolated human cell of claim 2, wherein an expression vector comprises the one or more polynucleotides.

4. The isolated human cell of claim 3, wherein the expression vector is a viral delivery vector.

5. The isolated human cell of claim 4, wherein the viral delivery vector is an adenovirus, a hybrid adenovirus or a non-integrating lentivirus.

6. A method of making an isolated human hematopoietic cell or T-cell with a cleaved GR gene, the method comprising contacting an isolated human hematopoietic or T-cell cell with the one or more polynucleotides of claim 2 such that the endogenous GR gene is cleaved and inactivated.

7. The isolated human cell of claim 1, wherein the cell is a T-cell or a hematopoietic cell.

* * * * *